(12) United States Patent
Neustadt et al.

(10) Patent No.: US 6,875,772 B2
(45) Date of Patent: Apr. 5, 2005

(54) [1,2,4]-TRIAZOLE BICYCLIC ADEONSINE A$_{2A}$ RECEPTOR ANTAGONISTS

(75) Inventors: Bernard R. Neustadt, West Orange, NJ (US); Hong Liu, Hackensack, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/304,939

(22) Filed: Nov. 26, 2002

(65) Prior Publication Data

US 2003/0191130 A1 Oct. 9, 2003

Related U.S. Application Data

(60) Provisional application No. 60/334,385, filed on Nov. 30, 2001.

(51) Int. Cl.$^7$ .................... C07D 487/04; A61K 31/519; A61P 25/24; A61P 25/16
(52) U.S. Cl. .................... 514/262.1; 544/263; 544/295; 544/324; 546/117
(58) Field of Search .................... 544/263; 514/262.1

(56) References Cited

U.S. PATENT DOCUMENTS 5,565,460 A    10/1996  Suzuki et al.

FOREIGN PATENT DOCUMENTS

| EP | 0 976 753 | * | 2/2000 |
| EP | 1 116 722 | * | 7/2001 |
| WO | WO 95/01356 |  | 1/1995 |
| WO | WO 97/05138 |  | 2/1997 |
| WO | WO98/52568 |  | 11/1998 |
| WO | WO 99/43678 |  | 9/1999 |
| WO | WO 01/17999 |  | 3/2001 |
| WO | WO 01/92264 |  | 12/2001 |

OTHER PUBLICATIONS

Vu et al. J. Med. Chem . . . 47 (2004). p. 4201–4299.*
Palmer, Biochemistry 36 (4) (1997). p. 832–838.*
Lazarino, Br. J. Pharmacol . . . 109 (4) (1993) pp. 1110–1119.*
"Parkinson's Treatments: L–dopa" <http://www.macalester.edu/~psych/whathap/UBNRP/parkinson/ldopa.html> downloaded from the Internet Jul. 15, 2004.*
"Understanding Parkinson's Disease" http://www.stalevo.com/info/simplystated/parkinsons_disease_treatment:jsp?checked=y downloaded from the Internet Jul. 15, 2004.*
Patent Abstract of Japan, vol. 2, No. 6 (2002), publication No. 2002037787, Feb. 6, 2002.*
Wermuth, "The Practice of Medicinal Chemistry," (Academic Press, 1996), p. 203–237.*
Ungerstedt et al, Brain Research, 24 (1970), 485–493.
Ungerstedt, Eur. J. Pharmacol., 5 (1968), 107–110.
Derwent Abstract of WO 99/43678.
U.S. Appl. No. 10/269,754, filed Oct. 11, 2002, Tulshian et al.

* cited by examiner

Primary Examiner—Mark L. Berch
(74) Attorney, Agent, or Firm—Anita W. Magatti

(57) ABSTRACT

Compounds having the structural formula I

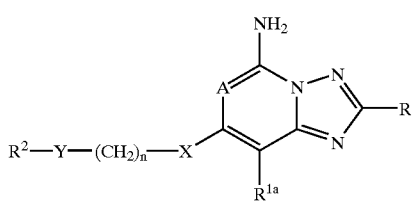

wherein:
n is 0, 1, 2 or 3;
A is C(R$^1$) or N;
R$^1$ and R$^{1a}$ are H, (C$_1$–C$_6$)-alkyl, halo, CN or —CF$_3$;
X is —C(O)—, —O—, —SO$_{0-2}$—, or optionally substituted methylene, imino, arylene or heteroaryldiyl;
Y is —O—, —SO$_{0-2}$—, or optionally substituted arylene, heteroaryldiyl, or nitrogen-containing heterocycloalkyl, or with certain provisos, a bond;
R is optionally substituted-aryl or heteroaryl; and
R$^2$ is optionally substituted aryl, heteroaryl, arylalkyl or heteroarylalkyl; or R$^2$—Y is a fused piperidinyl, substituted piperazinyl or substituted piperidinyl;
their use in the treatment of Parkinson's disease, alone or in combination with other agents for treating Parkinson's disease, pharmaceutical compositions comprising them and kits comprising the components of the combinations.

11 Claims, No Drawings

[1,2,4]-TRIAZOLE BICYCLIC ADEONSINE $A_{2A}$ RECEPTOR ANTAGONISTS

CROSS REFERENCE TO RELATED APPLICATION

This application claims the benefit of U.S. Provisional Application 60/334,385, filed Nov. 30, 2001.

BACKGROUND

The present invention relates to substituted [1,2,4]-triazole bicyclic adenosine $A_{2a}$ receptor antagonists, the use of said compounds in the treatment of central nervous system diseases, in particular Parkinson's disease, and to pharmaceutical compositions comprising said compounds.

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an antiaggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2a}$, $A_{2b}$ and $A_3$. $A_1$ and $A_3$ are high-affinity, inhibiting the activity of the enzyme adenylate cyclase, and $A_{2a}$ and $A_{2b}$ are low-affinity, stimulating the activity of the same enzyme. Analogs of adenosine able to interact as antagonists with the $A_1$, $A_{2a}$, $A_{2b}$ and $A_3$ receptors have also been identified.

Selective antagonists for the $A_{2a}$ receptor are of pharmacological interest because of their reduced level of side affects. In the central nervous system, $A_{2a}$ antagonists can have antidepressant properties and stimulate cognitive functions. Moreover, data has shown that $A_{2a}$ receptors are present in high density in the basal ganglia, known to be important in the control of movement. Hence, $A_{2a}$ antagonists can improve motor impairment due to neurodegenerative diseases such as Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2a}$ affinity with varying degrees of $A_{2a}$ vs. $A_1$ selectivity. Certain imidazolo- and pyrazolo-substituted triazolo-pyrimidine adenosine $A_{2a}$ receptor antagonists have been disclosed previously, for example in WO 95/01356; WO 97/05138; and WO 98/52568. Certain pyrazolo-substituted triazolo-pyrimidine adenosine $A_{2a}$ receptor antagonists are disclosed in U.S. Ser. No. 09/207,143, filed May 24, 2001. Certain imidazolo-substituted triazolo-pyrimidine adenosine $A_{2a}$ receptor antagonists are disclosed in U.S. Provisional Application 60/329,567, filed Oct. 15, 2001. U.S. Pat. No. 5,565,460 discloses certain triazolo-triazines as antidepressants; EP 0976753 and WO 99/43678 disclose certain triazolo-pyrimidines as adenosine $A_{2a}$ receptor antagonists; and WO 01/17999 discloses certain triazolo pyridines as adenosine $A_{2a}$ receptor antagonists.

SUMMARY OF THE INVENTION

The present invention relates to a compound represented by the structural formula I

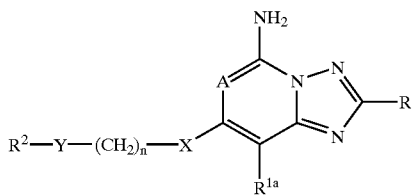

or a pharmaceutically acceptable salt thereof, wherein:

A is $C(R^1)$ or N;

$R^1$ and $R^{1a}$ are independently selected from the group consisting of H, $(C_1-C_6)$-alkyl, halo, CN and $-CF_3$;

Y is $-O-$, $-S-$, $-SO-$, $-SO_2-$, $R^5$-heteroaryldiyl, $R^5$-arylene or

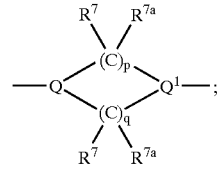

p and q are independently 2–3;

Q and $Q^1$ are independently selected from the group consisting of

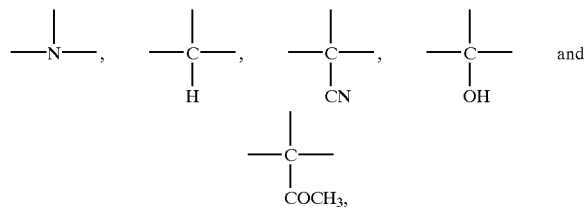

provided that at least one of Q and $Q^1$ is

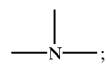

R is $R^5$-aryl, $R^5$-heteroaryl, $R^6-(C_2-C_6)$alkenyl or $R^6-(C_2-C_6)$alkynyl;

$R^2$ is $R^5$-aryl, $R^5$-heteroaryl, $R^5$-aryl$(C_1-C_6)$alkyl or $R^5$heteroaryl$(C_1-C_6)$alkyl; or $R^2-Y$ is

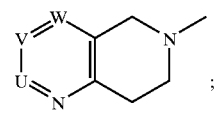

U, V, and W are independently selected from the group consisting of N and $CR^1$, provided that at least one of U, V and W is $CR^1$;

n is 1, 2 or 3; and (a) A is $C(R^1)$ and X is $-C(R^3)(R^{3a})-$, $-C(O)-$, $-O-$, $-S-$, $-SO-$, $-SO_2-$, $R^4$-arylene, $R^4$-heteroaryldiyl, or $-N(R^9)-$; or A is $C(R^1)$, Y is a bond, and X is $-C(R^3)(R^{3a})-$, $-C(O)-$, $-O-$, $-S-$, $-SO-$, $-SO_2-$, $R^4$-arylene, $-N(R^9)-$ or $R^4$-heteroaryldiyl, provided that when X is $-N(R^9)-$ or $R^4$-heteroaryldiyl, $R^2$ is not phenyl or phenyl-$(C_1-C_6)$alkyl; or (b) A is N, X is —N(R$^9$)—, Y is R$^5$-arylene and R$^2$ is

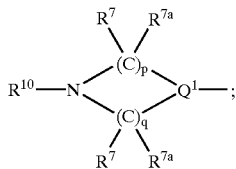

or n is 2 or 3; and (c) A is N and X is —C(R$^3$)(R$^{3a}$)—, —C(O), —O—, —S—, —SO—, —SO$_2$—, —N(R$^9$)—, R$^4$-arylene or R$^4$-heteroaryldiyl; or A is N, Y is a bond and X is —C(O)—, —N(R$^9$)—, R$^4$-arylene or R$^4$-heteroaryldiyl; or A is N, Y is —N(R$^{9a}$)—, —C(O)N(R$^{9a}$)— or —O—(CH$_2$)$_2$—N(R$^{9a}$)—, and X is —N(R$^9$)—; or A is N, X is —N(R$^9$)—, and Y and R$^2$ together are

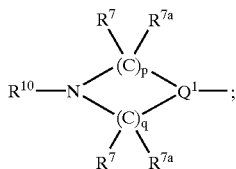

or n is 0; and (d) A is N, Y is a bond, X is —N(R$^9$)—, and R$^2$ is

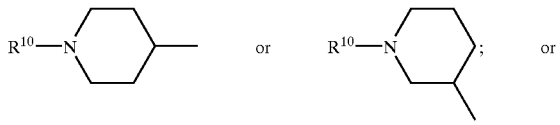

(e) A is N, X is —N(R$^9$)— and Y and R$^2$ together are

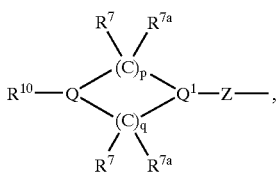

wherein Z is —C(O)—CH$_2$—, —C(O)—CH(C$_1$–C$_6$ alkyl)—, —CH$_2$—CH(C$_1$–C$_6$ alkyl)—, or —CH(C$_1$–C$_6$ alkyl)-CH$_2$—;

R$^3$ and R$^{3a}$ are independently selected from the group consisting of H, —OH, C$_1$–C$_6$ alkyl, hydroxy(C$_1$–C$_6$)alkyl, (C$_1$–C$_6$)alkoxy(C$_1$–C$_6$)alkyl, amino(C$_1$–C$_6$)alkyl, (C$_1$–C$_6$)alkylamino(C$_1$–C$_6$)alkyl and di(C$_1$–C$_6$)alkylamino(C$_1$–C$_6$)alkyl;

R$^4$ is 1–3 substituents selected from the group consisting of H, (C$_1$–C$_6$)alkyl, —OH, (C$_1$–C$_6$)alkoxy, (C$_1$–C$_6$)alkoxy(C$_1$–C$_6$)alkoxy, halo, —CF$_3$, and —CN;

R$^5$ is 1–3 substituents independently selected from the group consisting of H, (C$_1$–C$_6$)alkyl, —OH, (C$_1$–C$_6$)alkoxy, (C$_1$–C$_6$)alkoxy(C$_1$–C$_6$)alkyl, (C$_1$–C$_6$)alkoxy(C$_1$–C$_6$)-alkoxy, halo, —CF$_3$, —CN, —NH$_2$, (C$_1$–C$_6$)alkylamino, di(C$_1$–C$_6$)alkylamino, amino(C$_1$–C$_6$)-alkyl, (C$_1$–C$_6$)alkylamino(C$_1$–C$_6$)alkyl, di(C$_1$–C$_6$)alkylamino(C$_1$–C$_6$)alkyl, (C$_1$–C$_6$)alkanoyl-amino, (C$_1$–C$_6$)alkanesulfonylamino, (C$_1$–C$_6$)alkylthio, (C$_1$–C$_6$)alkylthio(C$_1$–C$_6$)alkyl, R$^6$—(C$_2$–C$_6$)alkenyl, R$^6$—(C$_2$–C$_6$)alkynyl, hydroxy(C$_1$–C$_6$)alkyl, (C$_1$–C$_6$)alkoxy-C(O)-amino, or heterocycloalkyl(C$_1$–C$_6$)alkyl;

R$^6$ is 1 to 3 substituents independently selected from the group consisting of H, —OH, (C$_1$–C$_6$)alkoxy and halo;

R$^7$ and R$^{7a}$ are independently selected from the group consisting of H, (C$_1$–C$_6$)alkyl, (C$_1$–C$_6$)alkoxy(C$_1$–C$_6$)alkyl, R$^8$-aryl and R$^8$-heteroaryl, or an R$^7$ and an R$^{7a}$ substituent on the same carbon can form =O;

R$^8$ is 1 to 3 substituents independently selected from H, (C$_1$–C$_6$)alkyl, —OH, (C$_1$–C$_6$)alkoxy, (C$_1$–C$_6$)alkoxy(C$_1$–C$_6$)alkoxy, halo, —CF$_3$, and —CN;

R$^9$ and R$^{9a}$ are independently selected from the group consisting of H, (C$_1$–C$_6$)alkyl, hydroxy(C$_2$–C$_6$)alkyl, (C$_1$–C$_6$)alkoxy(C$_2$–C$_6$)alkyl, amino(C$_2$–C$_6$)alkyl, (C$_1$–C$_6$)alkylamino(C$_2$–C$_6$)alkyl, di(C$_1$–C$_6$)alkylamino(C$_2$–C$_6$)alkyl, halo-(C$_3$–C$_6$)alkenyl, CF$_3$—(C$_1$–C$_6$)alkyl, (C$_3$–C$_6$)alkenyl, (C$_3$–C$_6$)cycloalkyl and (C$_3$–C$_6$)cycloalkyl-(C$_1$–C$_6$)alkyl, and R$^{10}$ is H, —C(O)—O—(C$_1$–C$_6$)alkyl, R$^5$-aryl, —C(O)—(C$_1$–C$_6$)alkyl, —C(O)—(R$^5$-aryl) or R$^5$-aryl-(C$_1$–C$_6$)alkyl.

Another aspect of the invention is a pharmaceutical composition comprising a therapeutically effective amount of at least one compound of formula I in a pharmaceutically acceptable carrier.

Yet another aspect of the invention is a method of treating central nervous system diseases such as depression, cognitive diseases and neurodegenerative diseases such as Parkinson's disease, senile dementia or psychoses of organic origin, or stroke, comprising administering at least one compound of formula I to a mammal in need of such treatment. In particular, the invention is drawn to the method of treating Parkinson's disease comprising administering at least one compound of formula I to a mammal in need of such treatment.

Still another aspect of the invention is a method of treating Parkinson's disease with a combination of at least one compound of formula I and one or more agents useful in the treatment of Parkinson's disease, for example dopamine; a dopaminergic agonist; an inhibitor of monoamine oxidase, type B (MAO-B); a DOPA decarboxylase inhibitor (DCI); or a catechol-O-methyltransferase (COMT) inhibitor. Also claimed is a pharmaceutical composition comprising at least one compound of formula I and one or more agents known to be useful in the treatment of Parkinson's in a pharmaceutically acceptable carrier. In the method comprising the administration of the combination of the invention, one or more compounds of formula I and one or more other anti-Parkinson's agents can be administered simultaneously or sequentially in separate dosage forms. Therefore, also claimed is a kit comprising in separate containers in a single package pharmaceutical compositions for use in combination to treat Parkinson's disease wherein one container comprises a pharmaceutical composition comprising an effective amount of a compound of formula I in a pharmaceutically acceptable carrier, and wherein, in separate containers, one or more pharmaceutical compositions each comprise an effective amount of an agent useful in the treatment of Parkinson's disease in a pharmaceutically acceptable carrier.

DETAILED DESCRIPTION

Referring to compounds of formula I above, preferred compounds of formula I are those wherein A is N. R is preferably furyl. R$^{1a}$ is preferably hydrogen. Another group of preferred compounds is that wherein X is —O—, —S—, —N(R$^9$)— or R$^4$-arylene, with compounds wherein X is —N(R$^9$)— being more preferred. R$^9$ is preferably C$_1$–C$_6$ alkyl, with methyl and ethyl being most preferred.

Preferred definitions for Y are a bond or piperazinyl (i.e., a group of the formula

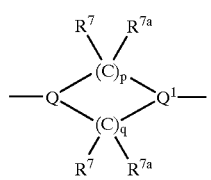

wherein Q and $Q^1$ are each nitrogen, p and q are each 2, and each $R^7$ and each $R^{7a}$ is H). $R^2$ is preferably $R^5$-aryl, more preferably $R^5$-phenyl.

When Y and/or $R^2$ is

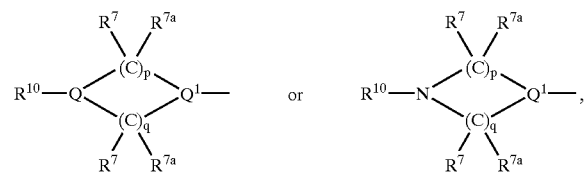

Q is preferably N, $Q^1$ is preferably N, p and q are each preferably 2, each $R^7$ and $R^{7a}$ is preferably hydrogen, and $R^{10}$ is preferably —C(O)—O—$(C_1$–$C_6)$alkyl, —C(O)—$(C_1$–$C_6)$alkyl or —C(O)—$(R^5$-aryl).

$R^5$ is preferably 1 or 2 substituents selected from the group consisting of H, $(C_1$–$C_6)$alkoxy, $(C_1$–$C_6)$alkoxy $(C_1$–$C_6)$-alkoxy, halo and —$CF_3$. More preferred are H, methoxy, methoxyethoxy, fluoro and chloro.

$R^4$ is preferably H, halo or $(C_1$–$C_6)$alkyl. $R^3$ and $R^{3a}$ are preferably independently selected from H and $(C_1$–$C_6)$alkyl. $R^{9a}$ is preferably H or $(C_1$–$C_6)$alkyl. $R^6$ is preferably hydrogen.

As used herein, the term alkyl includes saturated straight or branched carbon chains.

Halo means fluoro, chloro, bromo or iodo.

Alkenyl means a straight or branched hydrocarbon chain having at least one double bond. Similarly, alkynyl means a straight or branched hydrobcarbon chain having at least one triple bond.

Aryl means a single aromatic carbocyclic ring or a bicyclic fused carbocyclic ring of 6 to 10 carbon atoms, for example phenyl or naphthyl.

Heteroaryl means a single ring heteroaromatic group of 5 to 6 atoms comprised of 2 to 5 carbon atoms and 1 to 3 heteroatoms independently selected from the group consisting of N, O and S, or a bicyclic heteroaromatic group of 5 to 10 atoms comprised of 1 to 9 carbon atoms and 1 to 3 heteroatoms independently selected from the group consisting of N, O and S, provided that the rings do not include adjacent oxygen and/or sulfur atoms. Examples of single-ring heteroaryl groups are pyridyl, oxazolyl, isoxazolyl, oxadiazolyl, furanyl, pyrrolyl, thienyl, imidazolyl, pyrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1,5 or 1,7), imidazopyridyl, pyridopyrimidinyl and 7-azaindolyl. Also included in the definition of heteroaryl are benzofused heteroaryl groups comprising a heteroaryl ring as defined above fused at adjacent carbon atoms to a phenyl ring. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl. N-oxides of the ring nitrogens for all heteroaryl groups are also included. $R^4$- and $R^5$-substituted heteroaryl refers to such groups wherein substitutable ring carbon atoms have a substituent as defined above.

Heteroaryldiyl means a heteroaryl ring bonded to two different groups. For example, in the context of this invention, when Y is $R^5$-heteroaryldiyl, one ring member is attached to the group —$(CH_2)_n$—, and another ring member is attached to variable $R^2$; the $R^5$ substituents are attached to one or more of the remaining ring carbons. As an example, a pyridinediyl ring is shown:

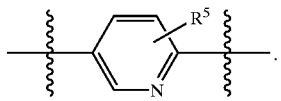

Similarly, arylene means a divalent aryl ring, that is, an aryl ring bonded to two different groups, e.g., phenylene.

Heterocycloalkyl means a 3 to 6-membered saturated ring comprised of 2 to 5 carbon atoms and 1 or 2 heteroatoms selected from the group consisting of N, S and O, provided that two heteroatoms are not adjacent to each other. Typical heterocycloalkyl rings are piperidinyl, piperazinyl, morpholinyl, azetidinyl, pyrrolidinyl, tetrahydrothienyl, tetrahydrofuranyl, tetrahydropyranyl and thiomorpholinyl.

When Y and/or $R^2$ comprise

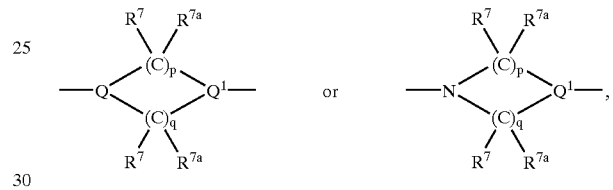

each $R^7$ and $R^{7a}$ substituent is independently selected from the groups included in the definition above; preferably no more than two of the substituents are other than hydrogen.

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a phenolic hydroxyl group. These compounds may form pharmaceutically acceptable salts. Examples of such salts may include sodium, potassium, calcium, aluminum, gold and silver salts.

Certain basic compounds also form pharmaceutically acceptable salts, e.g., acid addition salts. For example, pyrido-nitrogen atoms may form salts with strong acid, while compounds having basic functionality such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of formula I are prepared by general methods known in the art. Preferably, the compounds of formula I are prepared by the methods shown in the following reaction schemes. In the Schemes and examples that follow, the following abbreviations are used: Ph is phenyl, Me is methyl, Et is ethyl, TFA is trifluoroacetic acid, BSA is N,O-bis(trimethylsilyl)acetamide, DMF is dimethylformamide, EtOAc is ethyl acetate, THF is tetrahydrofuran, and DBU is 1,8-diazabicyclo[5.4.0]undec-7-ene.

Compounds of formula IIa where A is $C(R^1)$ can be prepared by methods described in application WO 01/11799. In addition, compounds wherein Y is not a bond can be prepared by methods illustrated in Scheme 1.

Where X is arylene, an intermediate of type 2 may be activated, e.g. to a chloride, which may then be reacted with a nucleophile 4 (e.g., Y=piperazinyl) to provide IIa. Alternatively, bromide 3 may be reacted with a nucleophile of type 5 provide IIa.

Compounds of formula IIb where A is N, and X is —O—, —S—, or —N($R^9$)— can be prepared by methods described in Schemes 2 and 3.

Scheme 1:

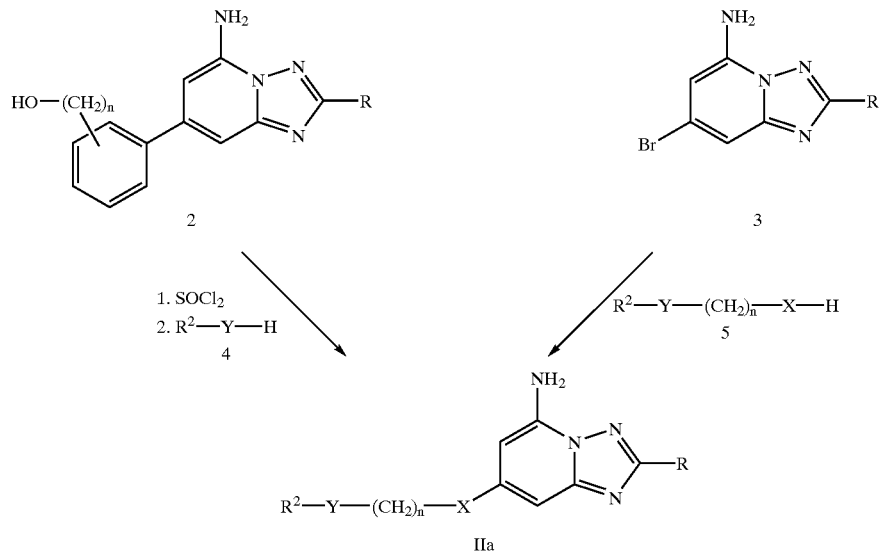

Scheme 2:

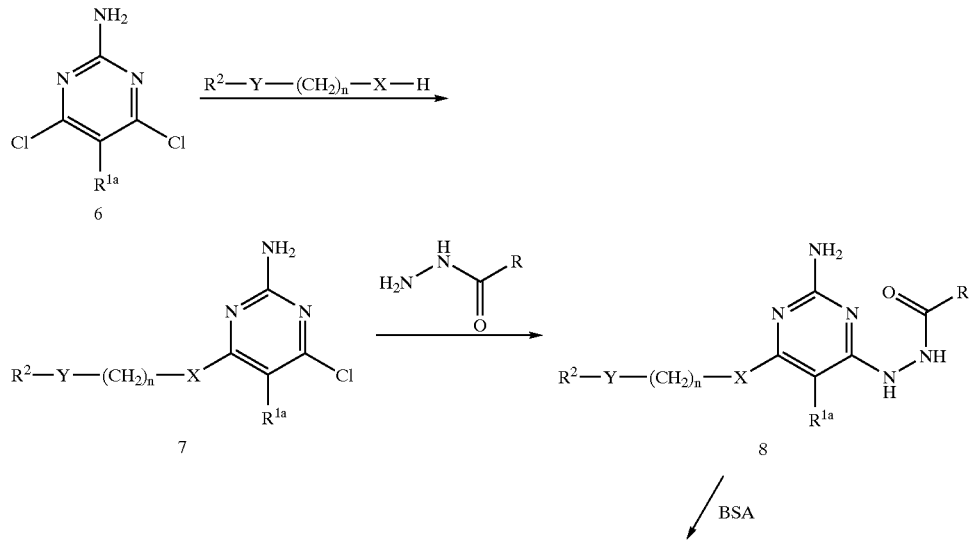

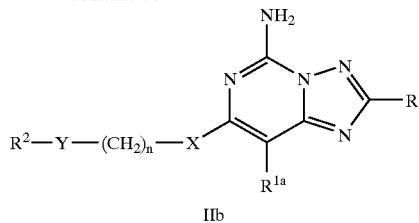

IIb

Chloride 6 is treated with an amine, alcohol or thiol in the presence of base to yield 7. Reaction with the appropriate hydrazide yields 8. Dehydrative cyclization with an agent such as BSA then yields the desired compound of formula IIb.

In a variant of this scheme, R in the hydrazide RCONHNH$_2$ may be a removable protective group such a t-butoxy or benzyloxy. In such a case, deprotection of 8 leads to 8a,

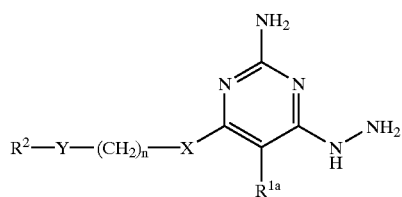

8a which may be acylated with RCOOH or the corresponding acid chloride, anhydride, or mixed anhydride. This produces a new 8, which may be converted to the desired compound of formula IIb.

In Scheme 3, the order of the steps is reversed in order to prepare compounds of formula IIb.

Scheme 3:

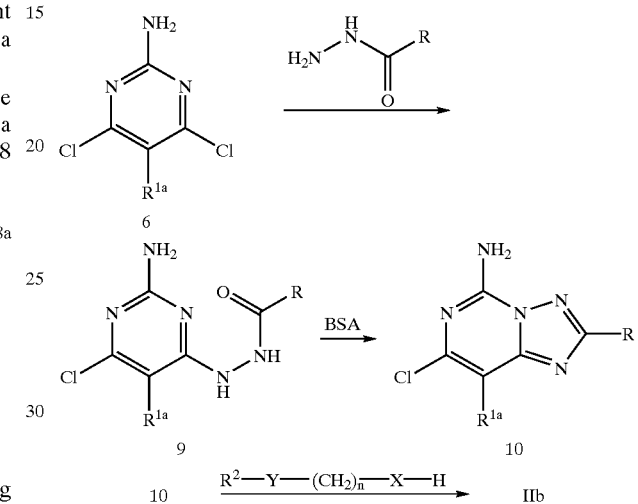

In Scheme 4, compounds of formula IIc, wherein A is N and X is —C(R$^3$)(R$^{3a}$)— are prepared.

Scheme 4:

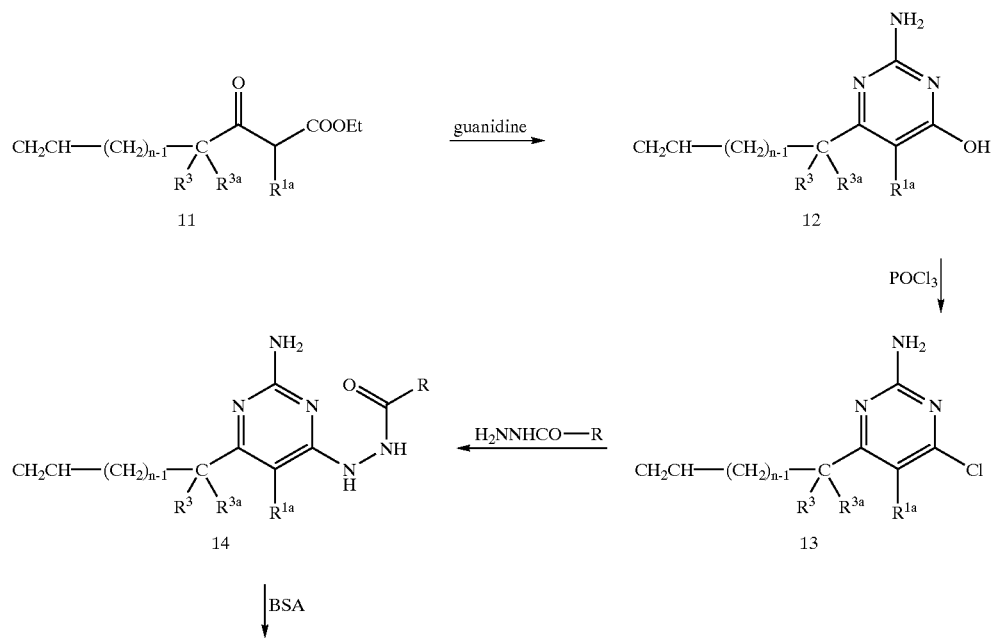

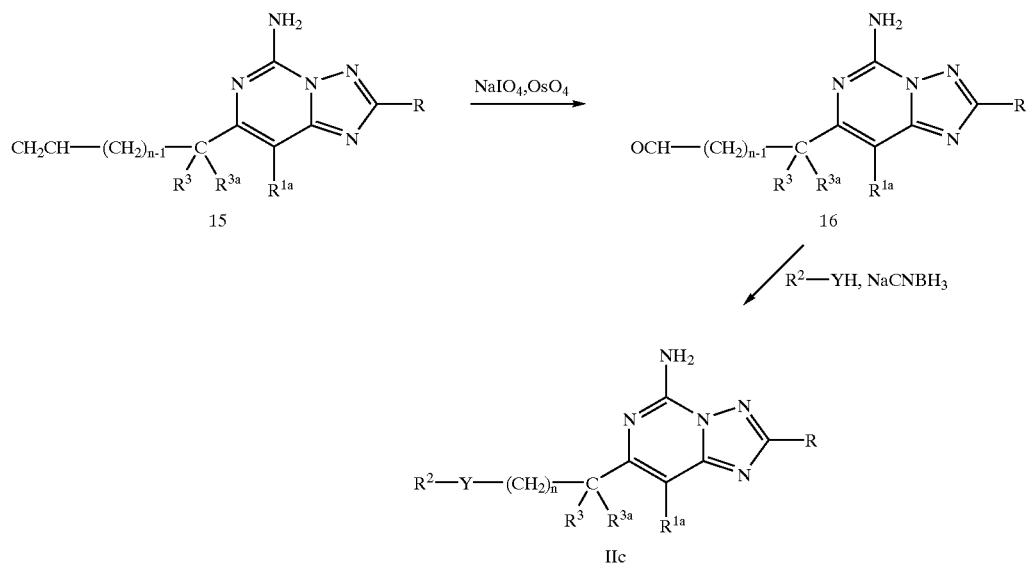

Keto-ester 11 is converted to pyrimidine 12, then to chloride 13. Reaction with a hydrazide provides 14, and BSA cyclization yields 15. The olefinic bond is cleaved to give aldehyde 16. When Y in IIc is linked to the alkylene chain through a nitrogen atom, reductive amination of 16 yields the desired compounds IIc.

A method of preparing compounds of formula IId or IIe where A is N and X is —S—, —SO— or —SO$_2$— is described in Scheme 5.

is employed to prepare the sulfoxide or sulfone of formula IIe.

For compounds IIf where $R^2$ contains an $R^{10}$ moiety, such moieties may be modified, as shown in Scheme 6. When $R^{10}$ is t-butoxycarbonyl or benzyloxycarbonyl or the like, the group may be converted to H, e.g. by treatment respectively with acid such as TFA or by hydrogenolysis. The resulting 17 may then be converted to a different compound IIf. For Scheme 5:

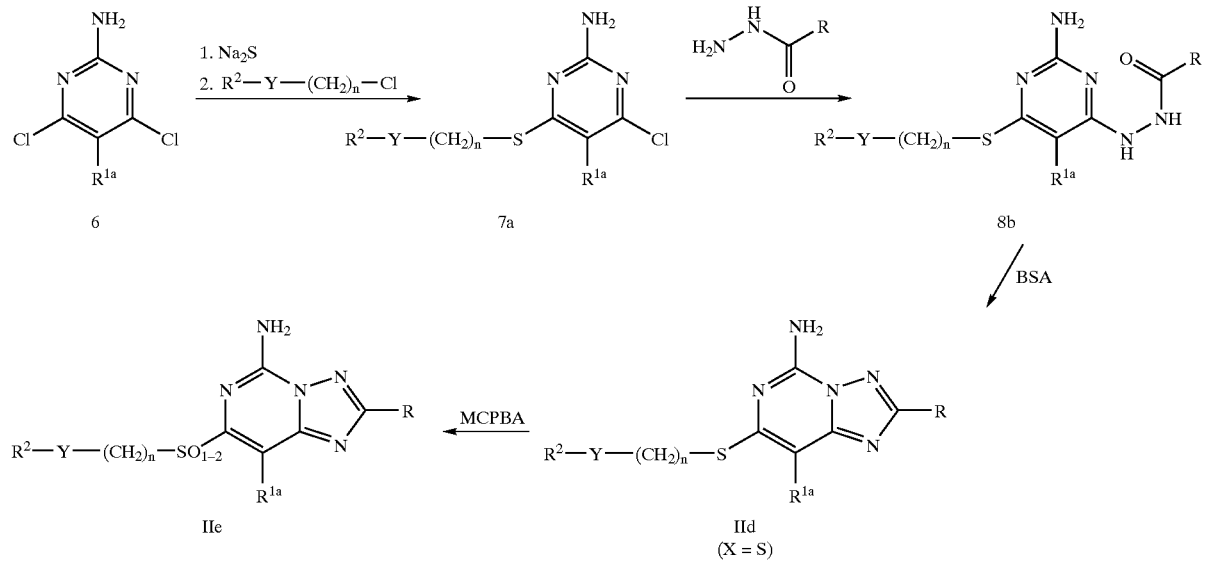

Chloride 6 is reacted with Na$_2$S and the intermediate then alkylated with a chloride or equivalent to give 7a. This is then converted to IId as in Scheme 2. Subsequent oxidation $R^{10}$=alkoxycarbonyl or aroyl, acylation may be achieved with an alkyl chloroformate or aroyl chloride or similar acylating agent. For $R^{10}$=aralkyl, reductive alkylation of 17 may be achieved with an aryl aldehyde and NaBH(OAc)$_3$.

Scheme 6:

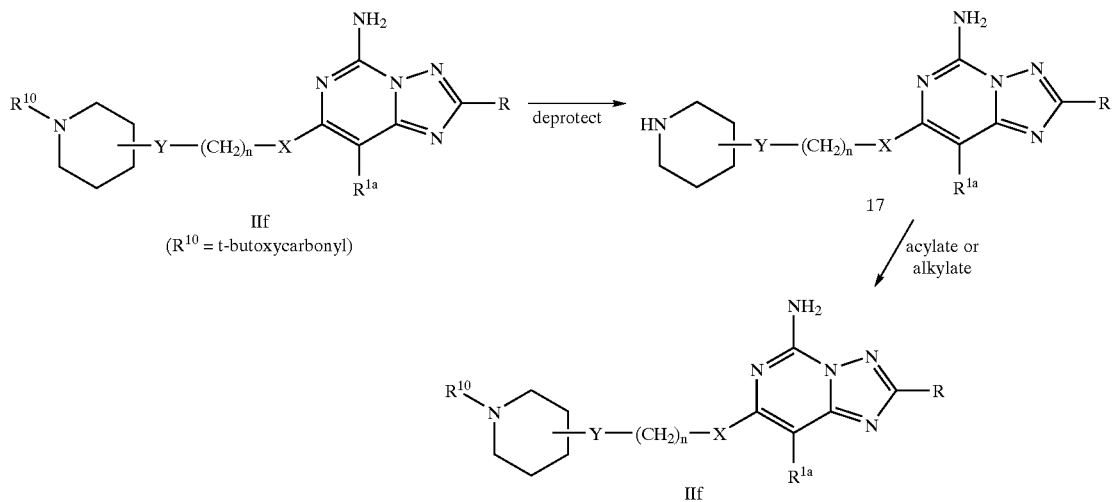

Similar methodology can be employed to prepare compounds of formula IIg:

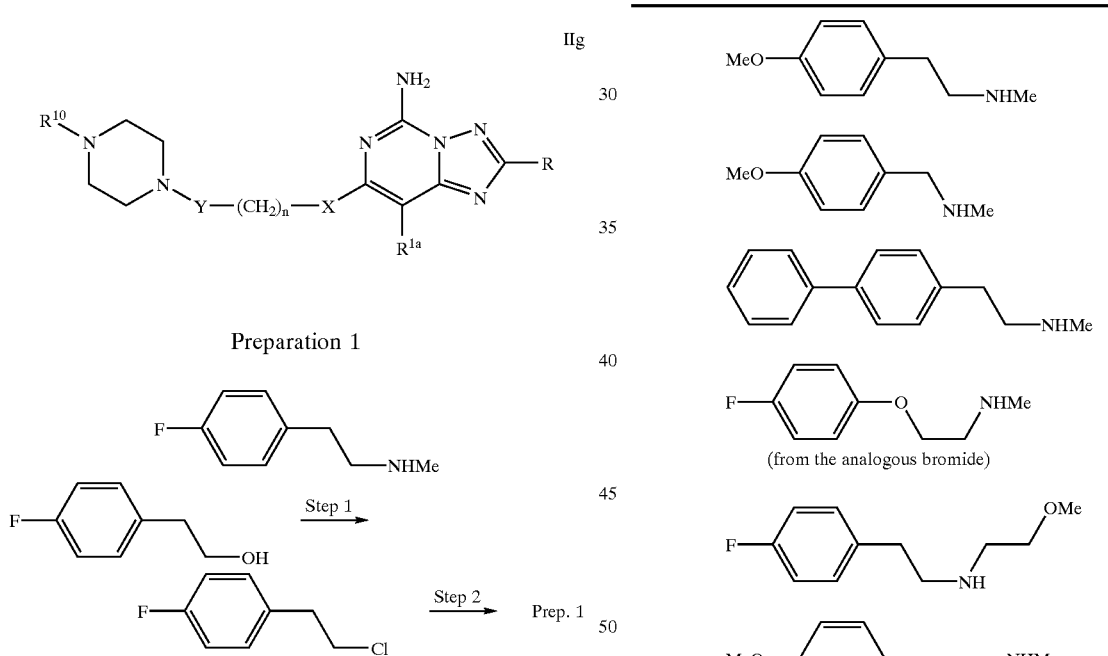

Preparation 1

Step 1: To 2-(4-fluorophenyl)ethanol (2.80 g, 20.0 mmol) add SOCl$_2$ (7.14 g, 60 mmol). Add two drops DMF and heat at 70° C. for 3 h. Concentrate, partition between hexane and ice-water, dry (MgSO$_4$), and concentrate to obtain the chloride as an almost colorless oil.

Step 2: Combine the chloride of Step 1 (1.00 g, 6.3 mmol) with 40% aqueous CH$_3$NH$_2$ (20 g, 260 mmol). Heat in a sealed tube at 65° C. for 2.5 h. Allow to cool, dilute with water, and extract with EtOAc. Extract the EtOAc with 0.5M HCl, basify with 20% NaOH, and extract with CH$_2$Cl$_2$. Dry (MgSO$_4$) and concentrate to obtain the title amine as a yellow oil.

Similarly, convert the corresponding alcohols to the following amines:

-continued

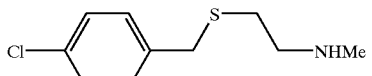

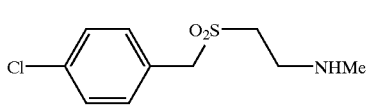

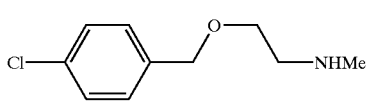

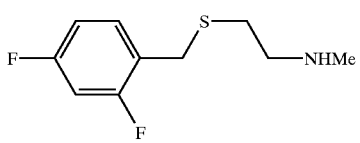

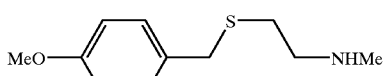

Similarly, convert the corresponding alcohols via the mesylates into the following amines:

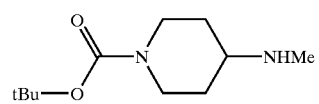

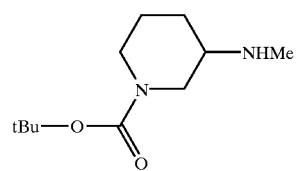

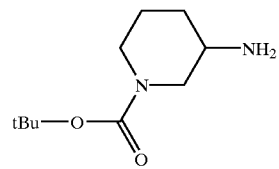

Preparation 2

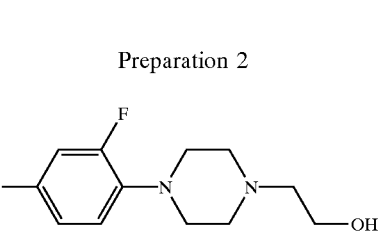

Combine 1-(2,4-difluorophenyl)piperazine (0.50 g, 2.5 mmol), 2-bromoethanol (0.37 g, 3.0 mmol), and Et₃N (0.30 g, 3.0 mmol) in THF (5 ml). Heat at reflux 4 h, allow to cool, and partition between water and CH₂Cl₂. Wash the CH₂Cl₂ with brine, dry (MgSO₄), and concentrate to obtain the title alcohol as a yellow oil.

Similarly prepare:

Prep. 2-2

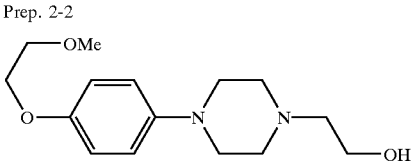

Prep. 2-3

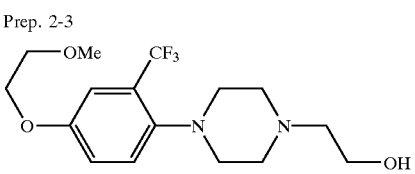

Prep. 2-4

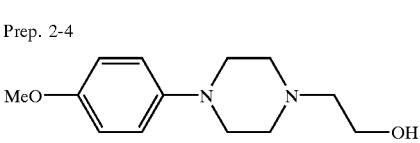

Prep. 2-5

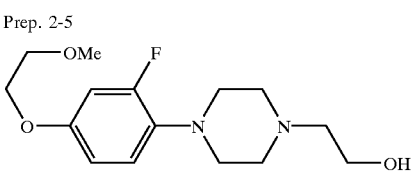

Prep. 2-6

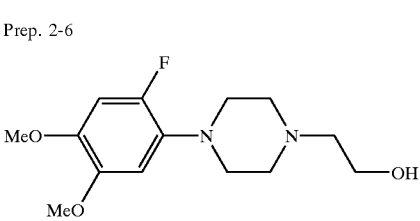

Prep. 2-7

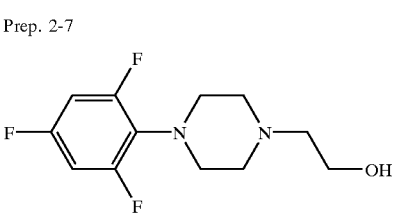

Prep. 2-8

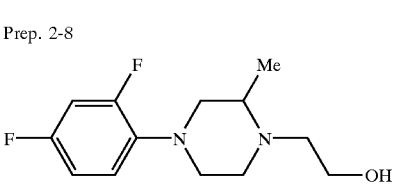

Prep. 2-9

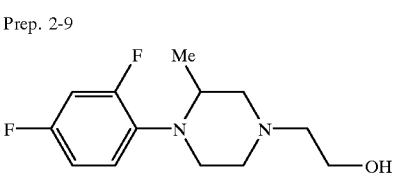

Preparation 3

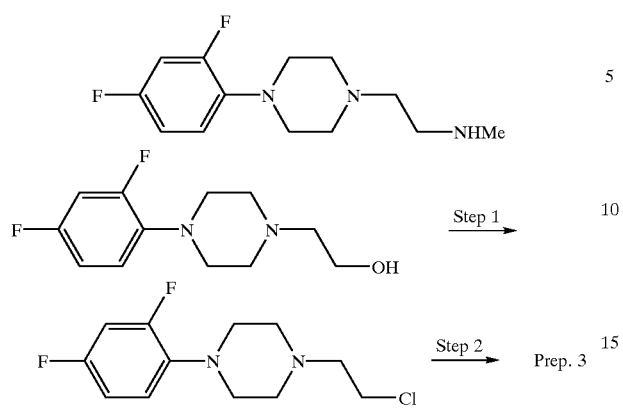

Step 1: To the product of Preparation 2 (0.50 g, 2.1 mmol) in $CH_2Cl_2$ (10 ml) add $SOCl_2$ (0.49 g, 4.2 mmol). Add two drops DMF and stir 4 h. Concentrate, partition between EtOAc and water, dry ($MgSO_4$), and concentrate to obtain the chloride as an almost colorless oil.

Step 2: Combine the product of Step 1 (0.51 g, 2.0 mmol) with 40% aqueous $CH_3NH_2$ (10 ml, 130 mmol) in EtOH (10 ml). Heat in a sealed tube at 80° C. for 2 h, allow to cool, concentrate, and partition between EtOAc and water. Dry ($MgSO_4$) and concentrate to obtain the title amine as a yellow oil.

Similarly prepare:

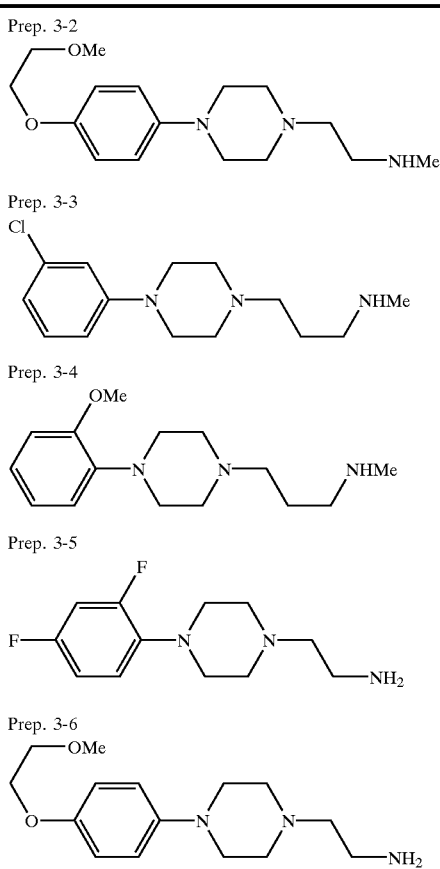

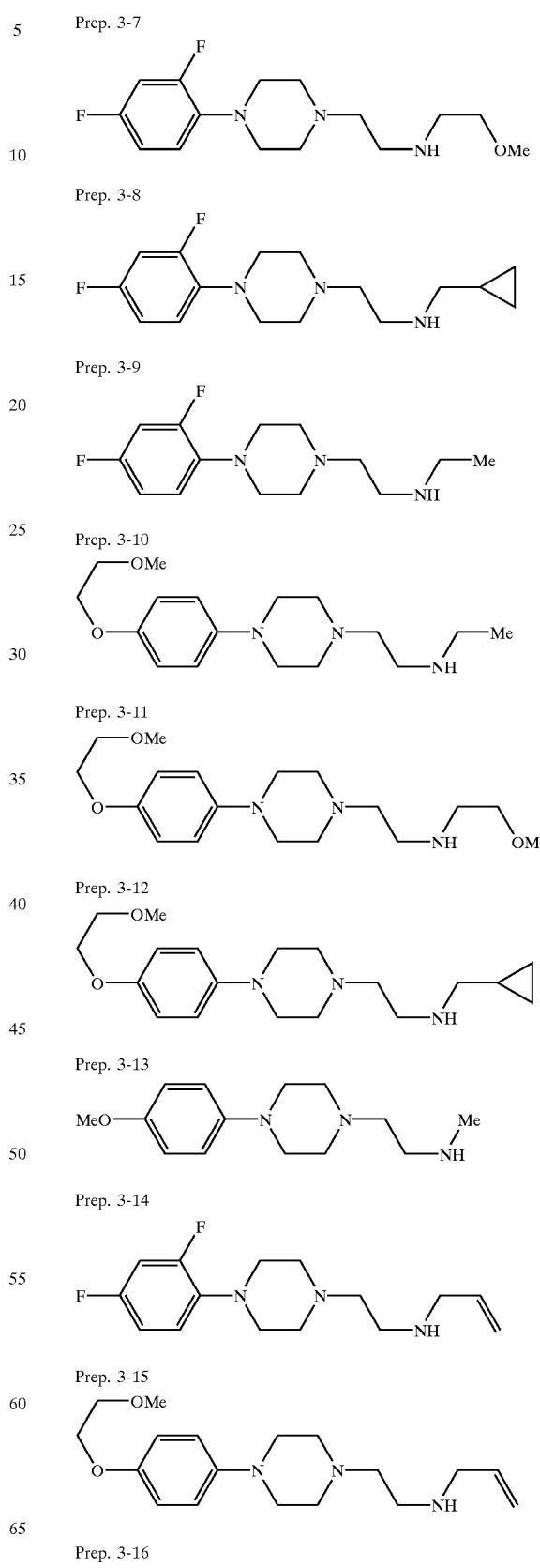

-continued
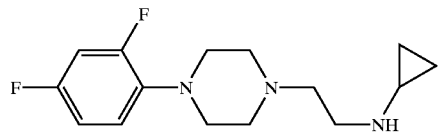
Prep. 3-17
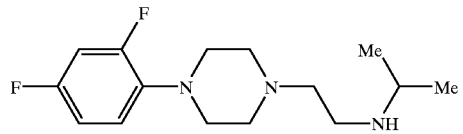
Prep. 3-18
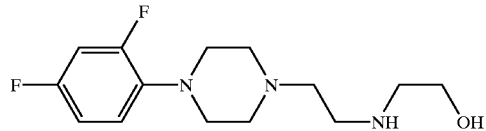
Prep. 3-19
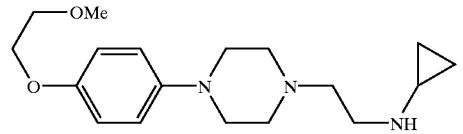
Prep. 3-20
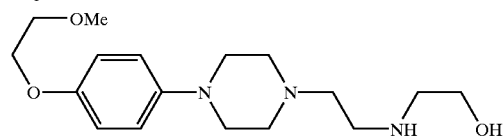
Prep. 3-21
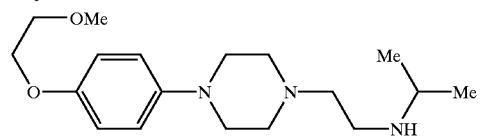
Prep. 3-22
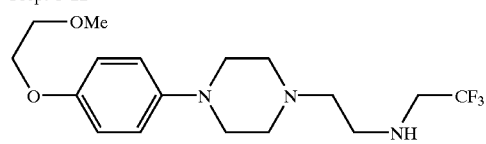
Prep. 3-23
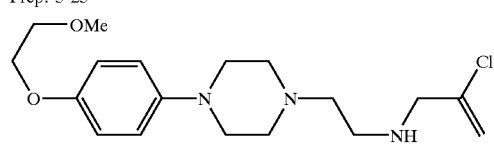
Prep. 3-24
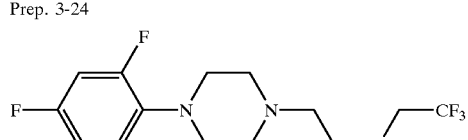
Prep. 3-25
-continued
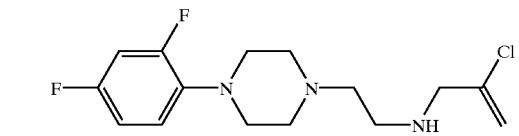
Prep. 3-26
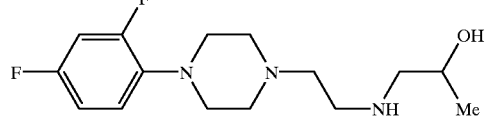
Prep. 3-27
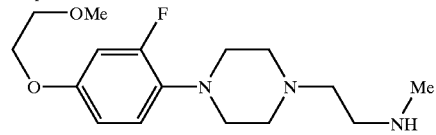
Prep. 3-28
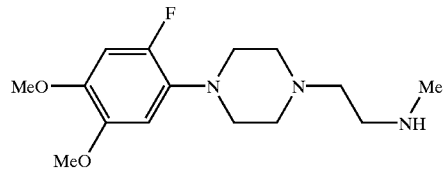
Prep. 3-29
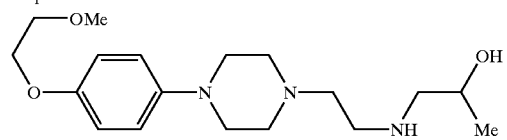
Prep. 3-30
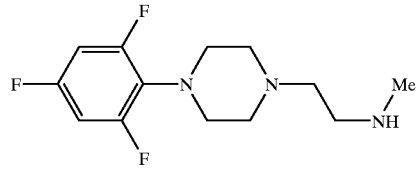
Prep. 3-31
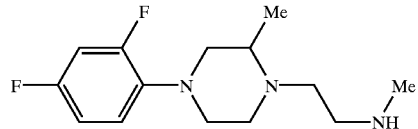
Prep. 3-32
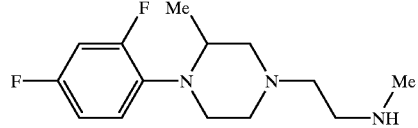
Prep. 3-33
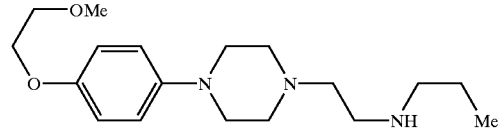
Prep. 3-34

-continued

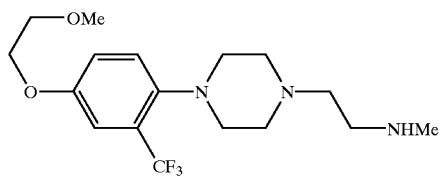

Preparation 4

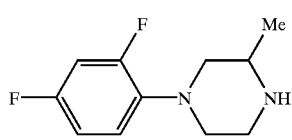

Combine 2,4-difluorobromobenzene (4.0 g, 20.7 mmol), 2-methylpiperazine (24.9 g, 249 mmol), NaO-tBu (2.79 g, 29.0 mmol), ±-BINAP (0.77 g, 1.2 mmol), and Pd$_2$(dba)$_3$ (0.24 g, 0.41 mmol) in toluene (40 ml). Heat at reflux 16 h, allow to cool, and extract with 1N HCl (4×50 ml). Basify with NaOH to pH 13 and extract with CH$_2$Cl$_2$. Dry (MgSO$_4$) and concentrate to give the product as a brown oil.

Preparation 5

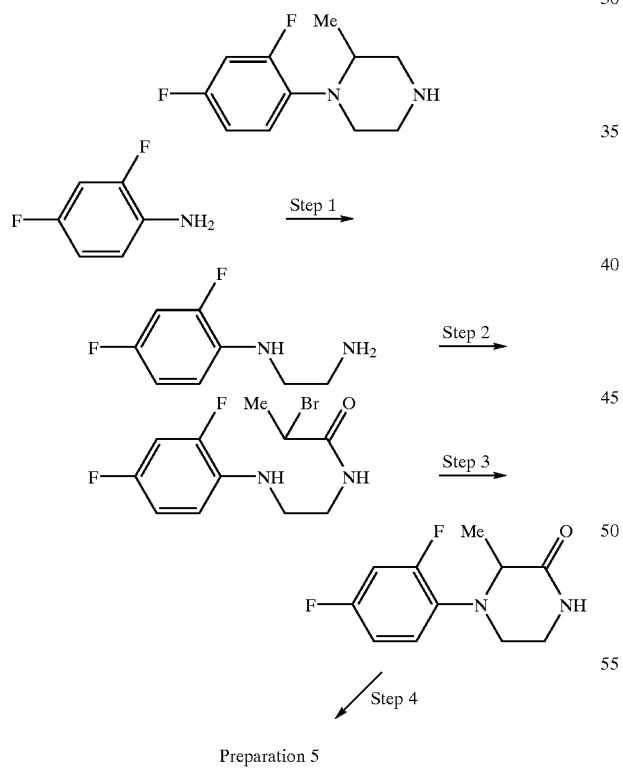

Preparation 5

Step 1: Combine 2,4-difluoroaniline (10.0 g, 77.4 mmol) and 2-bromoethylamine.HBr (15.9 g, 77.4 mmol) in toluene (100 ml). Heat at reflux 16 h, allow to cool, and remove the toluene layer. Dissolve the oily layer in water, basify with NaOH to pH 11, and extract with CH$_2$Cl$_2$. Dry (MgSO$_4$), concentrate, and distill at 120–30° C. (1 mm). Chromatograph on silica to obtain the product as a brown oil.

Step 2: Dissolve the product of Step 1 (3.0 g, 17 mmol) in CH$_2$Cl$_2$ (25 ml). Cool in ice and add Et$_3$N (5.3 ml, 38 mmol), followed by 2-bromopropionyl bromide (2.1 ml, 19 mmol). Allow to warm to RT, stir 16 h, cool in ice, and add more bromide (1.1 g) and Et$_3$N (1.0 g). Allow to warm to RT, stir 2 h, wash with water, dry (MgSO$_4$) and concentrate to obtain crude brown oil.

Step 3: Treat the product of Step 2 (5.86 g, 19 mmol) with DIPEA (2.97 g, 23 mmol) and KI (1.58 g, 9.5 mmol) in DMF (15 ml). Heat at 80° C. 18 h, allow to cool, concentrate and chromatograph on silica to obtain the product as a brown solid.

Step 4: Dissolve the product of Step 3 (1.33 g, 5.86 mmol) in THF (20 ml) and cool in ice. Add slowly 1.0M BH$_3$. THF solution (15 ml, 15 mmol). Allow to warm to RT, stir 1 h, add additional BH$_3$. THF solution (7 ml), and stir 2 h. Cool in ice and quench slowly with MeOH. Concentrate and partition with CH$_2$Cl$_2$ and 0.5N NaOH. Dry (MgSO$_4$), concentrate and purify by PLC to obtain the title compound as a yellow oil.

Preparation 6

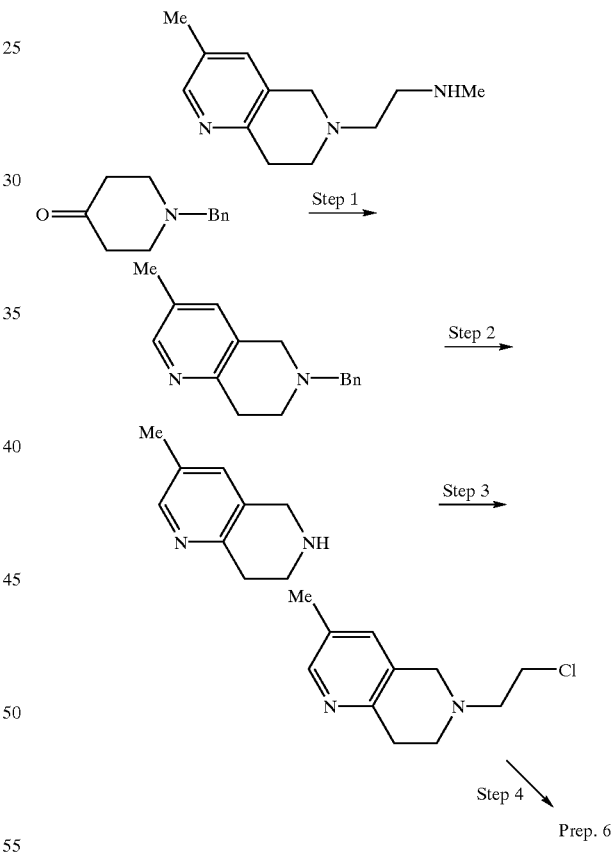

Step 1: Combine N-benzyl-4-piperidone (3.57 ml, 20 mmol), 3-ethoxymethacrolein (3.76 ml, 30 mmol), NH$_4$OAc (0.82 g, 11 mmol), and 28% aqueous ammonia (4.17 ml, 62 mmol). Heat in a sealed tube at 90° C. 48 h, allow to cool, and partition between Et$_2$O and 1N NaHCO$_3$. Extract the Et$_2$O with 1N HCl and basify the extract with NaOH to pH 13. Extract with Et$_2$O, dry (MgSO$_4$) and concentrate. Subject the oil to Kugelrohr distillation at 0.5 mm, collecting 90–160° C. to obtain the product as an orange oil.

Step 2: Dissolve the product of Step 1 (1.73 g, 7.3 mmol) in 10:1 MeOH/conc. HCl (44 ml). Add 10% Pd/C (0.40 g) and hydrogenate at 60 psi for 18 h. Filter through Celite and concentrate to solid. Dissolve in 95% EtOH and add NaOtBu (0.70 g). Concentrate, treat with etOH, filter, and concentrate to leave the crude product as a yellow solid.

Step 3: Combine the product of Step 2 (0.200 g, 1.35 mmol), 1-bromo-2-chloroethane (0.45ml, 5.4 mmol), and DIPEA (0.28 ml, 1.6 mmol) in DMF (10 ml). Stir48 h, add 1N NaOH (5 ml), and extract with Et$_2$O. Dry (MgSO$_4$), concentrate and purify by PLC to obtain the product as a yellow oil.

Step 4: Combine the product of Step 3 (0.22 g, 1.0 mmol), with 40% aqueous MeNH$_2$ (5.0 ml) and EtOH (5 ml). Heat in a sealed tube at 100° C. 3 h, allow to cool, add 1N NaOH (3 ml), concentrate and partition between CH$_2$Cl$_2$ and water. Dry (MgSO$_4$), and concentrate to obtain the title compound as a light brown oil.

Preparation 7

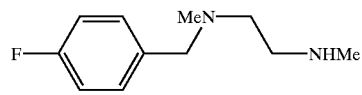

Combine 4-fluorobenzyl chloride (1.74 g, 12.0 mmol), N,N'-dimethylethylene-diamine (3.17 g, 36 mmol), KI (0.20 g, 1.2 mmol), and NaHCO$_3$ (1.51 g, 18 mmol) in EtOH (20 ml). Heat at reflux 4 h, filter, and concentrate. Partition with 1N HCl and EtOAc and basify the aqueous layer with NaOH. Extract with CH$_2$Cl$_2$, dry (MgSO$_4$), and concentrate. Distill at 0.5 mm up to 100° C. to obtain the title compound as a colorless liquid.

Preparation 8

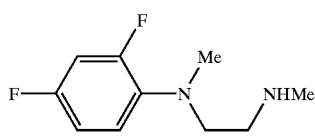

Combine 2,4-difluorfluoro-N-methylaniline (1.00 g, 6.98 mmol) and 4M HCl/dioxane (10 ml) in MeOH (10 ml). Concentrate to a white solid. Add 3-methyl-2-oxazolidinone (0.60 g, 6.98 mmol). Heat at 160° C. 18 h. Allow to cool, basify with NaOH, and extract with CH$_2$Cl$_2$. Dry (MgSO$_4$), concentrate, and chromatograph on silica to obtain the title compound as a yellow oil. This contains some of the product with aniline methyl removed.

EXAMPLE 1

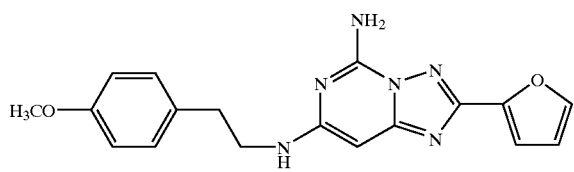

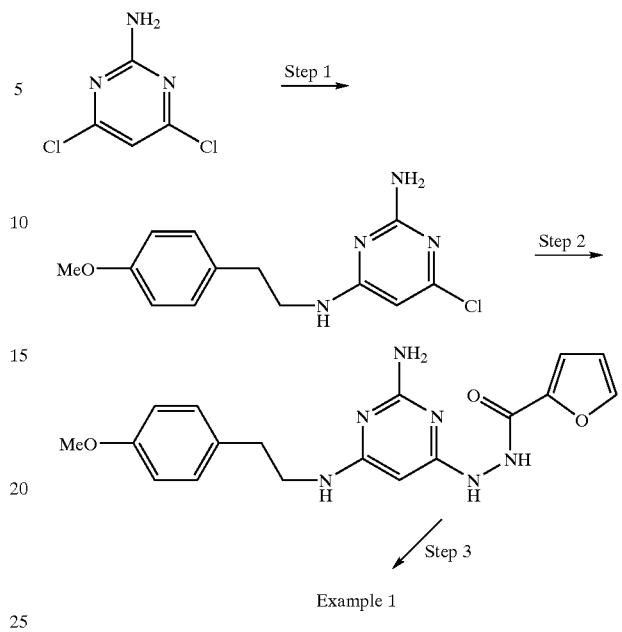

Example 1

Step 1: Combine 2-amino-4,6-dichloropyrimidine (0.50 g, 3.0 mmol), 2-(4-methoxy-phenyl)ethylamine (0.51 g, 3.4 mmol) and K$_2$CO$_3$ (0.46 g, 3.4 mmol e) in EtOH (8 ml). Heat in a sealed tube at 90° C. 1 h. Stir another 16 h, dilute with water (15 ml), filter, and purify on PLC to obtain the chloropyrimidine as a white solid.

Step 2: Combine the product of Step 1 (0.30 g, 1.08 mmol), 2-furoic hydrazide (0.16 g, 1.3 mmol),and 1.0 N HCl (0.4 ml) in EtOH (3 ml). Heat in a sealed tube at 90° C. for 16 h. Basify with NH$_3$, extract with EtOAc, and purify on PLC to obtain the hydrazide as a yellow solid.

Step 3: Add the product of Step 2 to BSA (4.0 ml). Heat at 120° C. 18 h. Pour into CH$_3$OH, concentrate, and purify on PLC to obtain the title compound as a white solid, MS: m/e 351 (M+1).

In a similar manner, prepare the following compounds (Et$_3$N employed as base in Step 1):

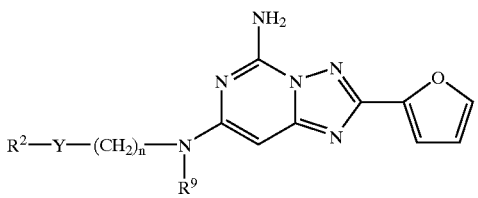

wherein R$^2$—Y—(CH$_2$)$_n$—N(R$^9$)— is as defined in the table:

| Example | R²—Y—(CH₂)ₙ—N(R⁹)— | MS m/e |
|---|---|---|
| 1-2 | MeO–C₆H₄–CH₂CH₂–N(Me)Me | 365 |
| 1-3 | 2,4-F₂-C₆H₃–piperazine–CH₂CH₂–N(Me)Me | 455 |
| 1-4 | Ph–C₆H₄–CH₂CH₂–N(Me)Me | 411 |
| 1-5 | F–C₆H₄–CH₂CH₂–N(Me)Me | 353 |
| 1-6 | F–C₆H₄–CH₂CH₂–N(Me)Et | 367 |
| 1-7 | 4-F–C₆H₄–O–CH₂CH₂–N(Me)Me | 369 |
| 1-8 | F–C₆H₄–CH₂CH₂–N(Me)CH₂CH₂OMe | 397 |
| 1-9 | 4-H₃CO–C₆H₄–CH₂CH₂CH₂–N(Me)Me | 379 |
| 1-10 | 3-Cl–C₆H₄–piperazine–CH₂CH₂CH₂–N(Me)Me | 467, 469 |
| 1-11 | 2-MeO–C₆H₄–piperazine–CH₂CH₂CH₂–N(Me)Me | 463 |

-continued

| Example | R²—Y—(CH₂)ₙ—N(R⁹)— | MS m/e |
|---|---|---|
| 1-12 | 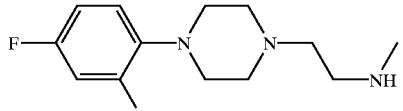 | 441 |
| 1-13 | 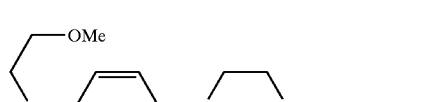 | 479 |
| 1-14 | 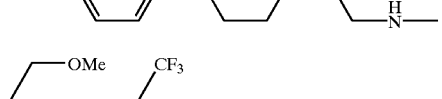 | 561 |

Similarly, by employing benzoic hydrazide in place of furoic hydrazide, prepare Example 1–15 as a yellow solid.

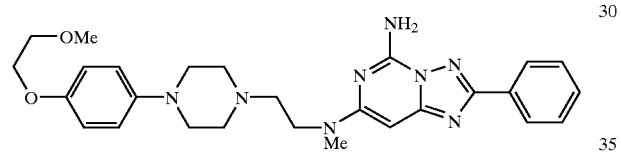

1–15: MS: m/e 503 (M + 1)

EXAMPLE 2

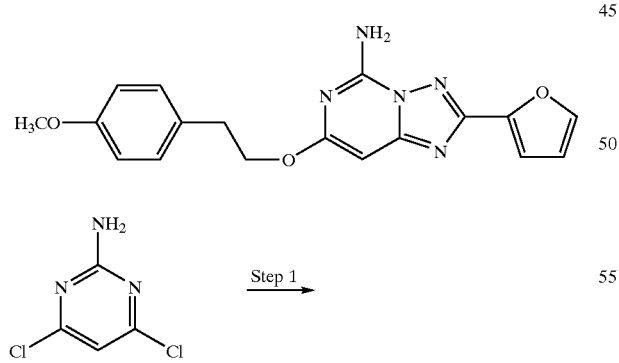

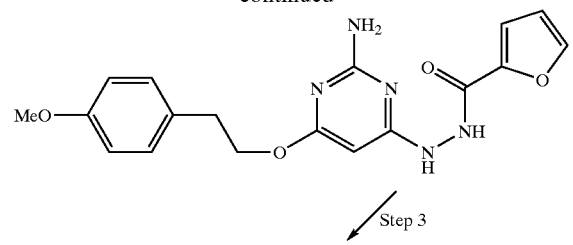

Step 1: To NaH (60% in oil, 0.16 g, 4.0 mmol) in THF (6 ml) add 2-(4-methoxy-phenyl)ethanol (0.46 g, 3.0 mmol). Stir 0.5 h and add 2-amino-4,6-dichloro-pyrimidine (0.50 g, 3.0 mmol). Heat at reflux 24 h. Filter, wash with CH₂Cl₂, concentrate, and purify on PLC to obtain the chloropyrimidine as a white solid.

Conduct Steps 2 and 3 as in Example 1 to obtain the title compound as a white solid, MS: m/e 352 (M+1).

In a similar manner prepare the following:

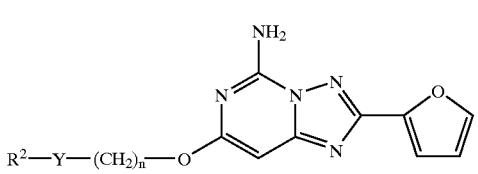

wherein R²—Y—(CH₂)ₙ—O— is as defined in the table:

| Example | R²—Y—(CH₂)ₙ—O— | MS m/e |
|---|---|---|
| 2-2 |  | 366 |

-continued

| Example | R²—Y—(CH₂)ₙ—O— | MS m/e |
|---|---|---|
| 2-3 | 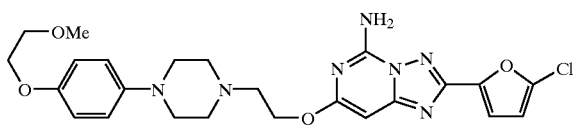 | 442 |
| 2-4 | | 398 |
| 2-5 | | 480 |
| 2-6 | | 548 |

Similarly, by employing 5-chloro-2-furoic hydrazide in place of furoic hydrazide, prepare Example 2–7 as a yellow solid:

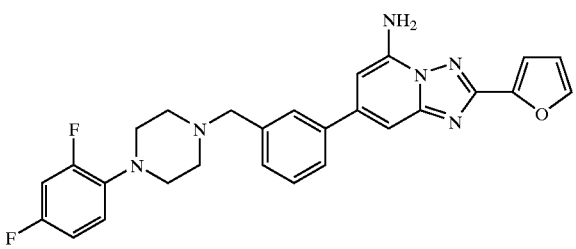

2–7: MS m/e 514, 516 (M + 1)

EXAMPLE 3

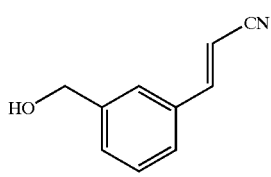

Step 1:

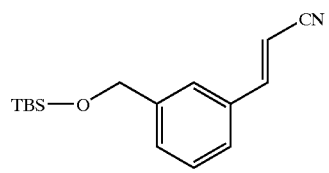

Combine 3-iodobenzyl alcohol (2.00 g, 8.5 mmol), acrylonitrile (0.67 ml, 10.2 mmol), and Et₃N (4.3 ml, 26 mmol) in DMF (30 ml). Purge with N₂ and add (Ph₃P)₂PdCl₂ (0.12 g, 0.17 mmol). Heat in a sealed vessel 3 days at 120°, allow to cool, and partition between CH₂Cl₂ and sat. NaHCO₃. Dry (MgSO₄) and concentrate. Chromatograph on silica to obtain the nitrile as a yellow oil.

Step 2:

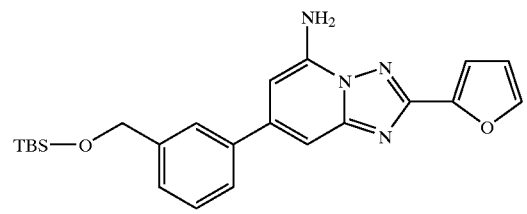

Combine the product of Step 1 (1.25 g, 7.9 mmol), t-butyldimethylsilyl chloride (1.42 g, 9.4 mmol), and imidazole (0.69 g, 10.2 mmol) in DMF (15 ml). Stir 7 h, partition between Et₂O and water, dry the Et₂O (MgSO₄) and concentrate to obtain the silyl ether as a colorless oil.

Step 3:

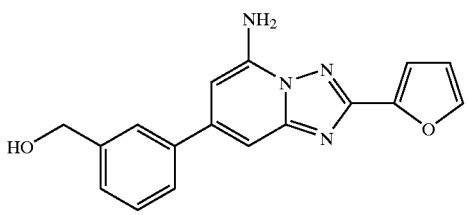

To a boiling suspension of potassium t-butoxide (2.34 g, 24.4 mmol) in THF (20 ml) add dropwise over 5 h a solution of the product of Step 2 (2.15 g, 7.9 mmol) and 3-(2-furyl)-5-phenylsulfonylmethyl[1,2,4]triazole (2.27 g, 7.9 mmol) in THF (20 ml). Heat 18 h, allow to cool, add water (30 ml), and extract 3× with 5% CH₃OH/CH₂Cl₂. Dry (MgSO₄), concentrate, and chromatograph on silica to obtain the bicyclic as a yellow solid.

Step 4:

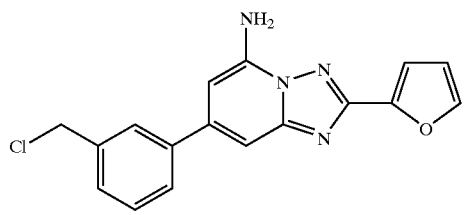

To the product of Step 3 (0.75 g, 1.8 mmol) in THF (5 ml) add tetrabutyl-ammonium fluoride (1.0M in THF, 2.14 ml). Stir 2 h, concentrate, and purify on PLC to obtain the alcohol as a yellow solid.

Step 5:

To the product of Step 4 (0.200 g, 0.65 mmol) in CH₂Cl₂ (10 ml) add SOCl₂ (0.19 ml, 2.6 mmol) and two drops pyridine. Heat at reflux 1 h, allow to cool, wash with 1N NaOH, concentrate, dry (MgSO₄), and concentrate to obtain the crude chloride as a yellow solid.

Step 6: Combine the product of Step 5 (0.090 g, 0.28 mmol) with 1-(2,4-difluoro-phenyl)piperazine (0.065 g, 0.33 mmol) and diisopropylethylamine (0.058 ml) in DMF (4 ml). Stir 3 days, heat to 60° for 3 h, allow to cool, concentrate, and purify on PLC to obtain the title compound as a white solid: MS m/e=487 (M+1).

In similar fashion, employ 1-(4-(2-methoxyethoxy)phenyl)piperazine to obtain Example 3-2 as a white solid.

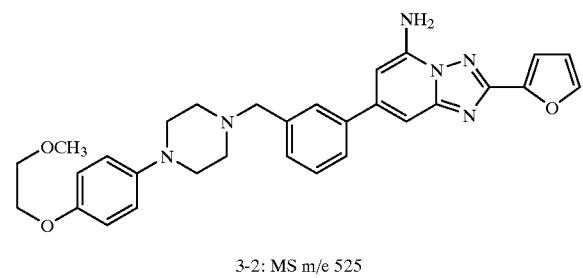

3-2: MS m/e 525

EXAMPLE 4

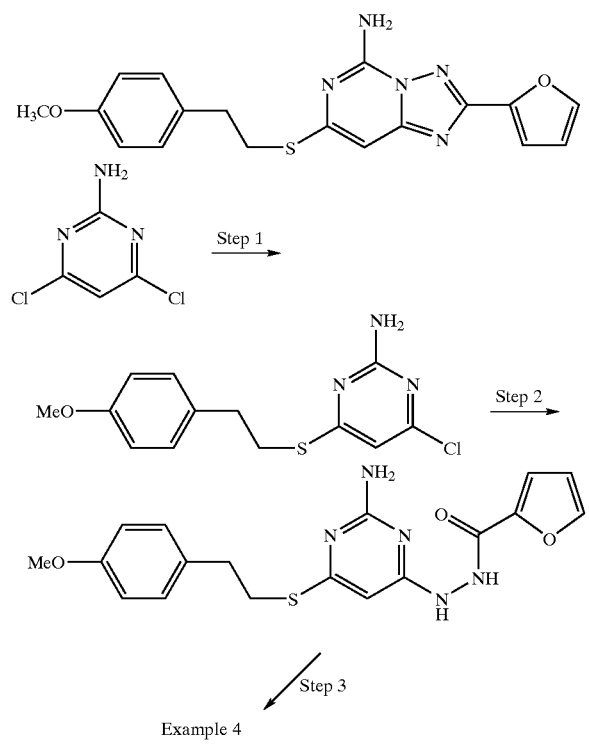

Example 4

Step 1: Combine 2-amino-4,6-dichloropyrimidine (0.50 g, 3.0 mmol) and $Na_2S$ (0.29 g, 3.7 mmole) in DMF (6 ml). Stir for 1 h. Add 4-methoxyphenethyl chloride (0.64 g, 3.77 mmol) and heat at 80° C. 18 h. Add water and extract with EtOAc. Purify on PLC to obtain the chloropyrimidine as a white solid.

Steps 2 and 3: Conduct as for Example 1, Steps 2 and 3, to obtain the title compound as a white solid, MS: m/e 368 (M+1).

In a similar manner, from the products of Preparation 3-2, Step 1, and Preparation 3–6, Step 1, prepare the following:

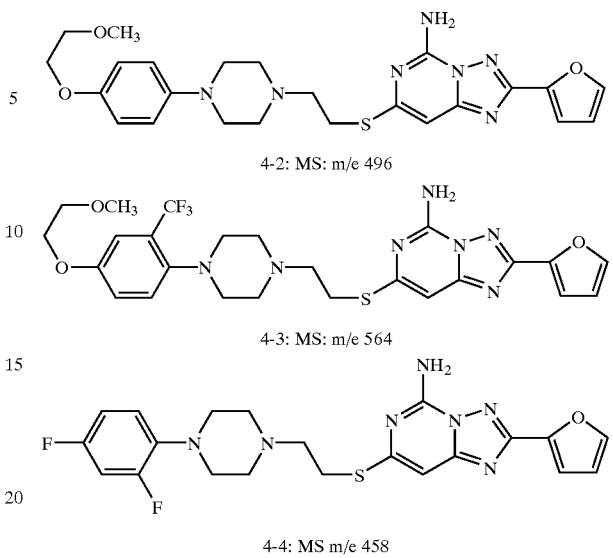

4-2: MS: m/e 496

4-3: MS: m/e 564

4-4: MS m/e 458

EXAMPLE 5

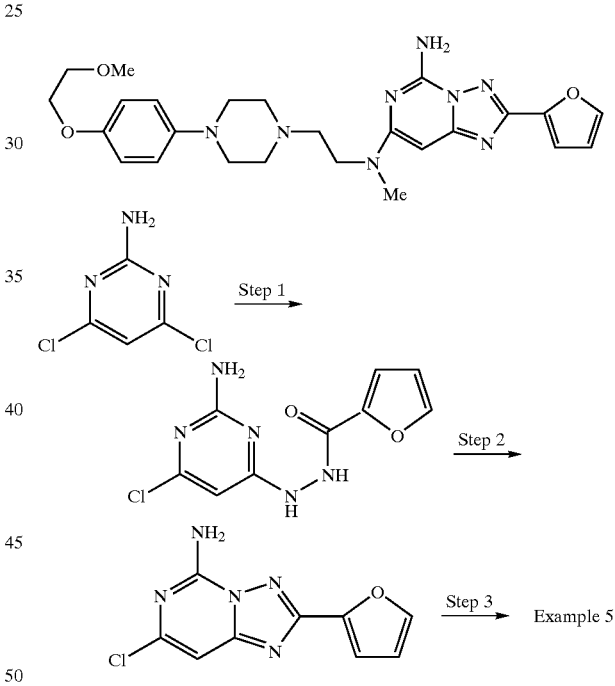

Step 1: Combine 2-amino-4,6-dichloropyrimidine (1.00 g, 6.10 mmol), 2-furoic hydrazide (0.97 g, 7.7 mmol) and $K_2CO_3$ (1.13 g, 8.2 mmole) in EtOH (6 ml). Heat in a sealed tube at 100° C. 18 h. Allow to cool, filter, wash with water to obtain product. Extract the filtrate with EtOAc, concentrate and recrystallize from EtOAc to obtain additional product as a yellow solid.

Step 2: Add the product of Step 1 (0.50 g, 2.13 mmol) to BSA (15 ml). Heat at 120° C. 18 h, allow to cool, and pour into $CH_3OH$ (20 ml). Concentrate and heat at reflux in 50% EtOH (40 ml) 1 h. Remove EtOH and extract with $CH_2Cl_2$. Dry and concentrate to obtain the product as a white solid.

Step 3: Combine the product of Step 2 (0.093 g, 0.39 mmol), the product of Preparation 3-2 (0.127 g, 0.43 mmol), and DBU (0.059 ml, 0.42 mmol) in DMF (2 ml). Heat at 140° C. 2 h, concentrate and purify on PLC to obtain the title compound as a yellow solid, MS: m/e 493 (M+1).

In a similar manner, employing the appropriate amine from Preparation 1 or Preparation 3, prepare the following:

| Example | R²—Y—(CH₂)ₙ—N(R⁹)— | MS m/e |
|---|---|---|
| 5-2 | 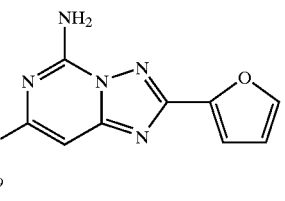 | 339 |
| 5-3 | 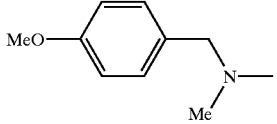 | 499 |
| 5-4 | 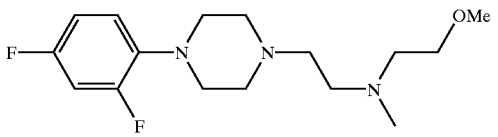 | 495 |
| 5-5 | 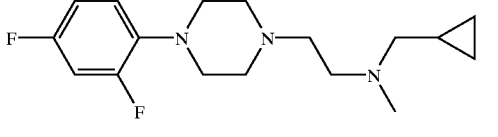 | 469 |
| 5-6 | 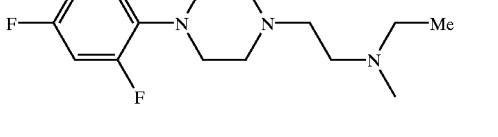 | 507 |
| 5-7 | 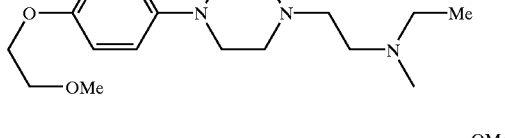 | 537 |
| 5-8 | 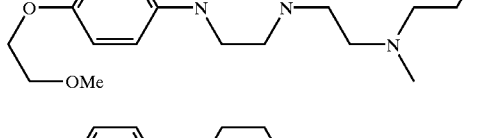 | 533 |
| 5-9 | 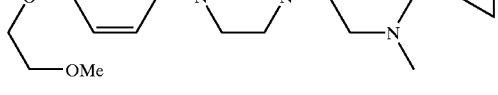 | 449 |
| 5-10 | 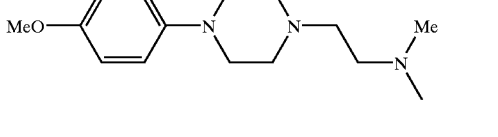 | 481 |

-continued
| Example | R²—Y—(CH₂)ₙ—N(R⁹)— | MS m/e |
|---|---|---|
| 5-11 | 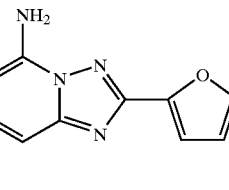 | 519 |
| 5-12 | 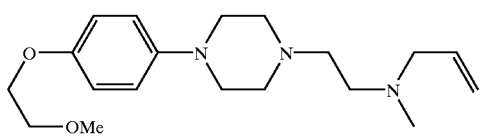 | 481 |
| 5-13 | 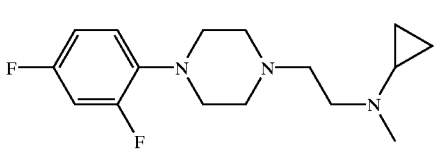 | 483 |
| 5-14 | 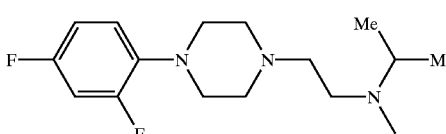 | 485 |
| 5-15 | 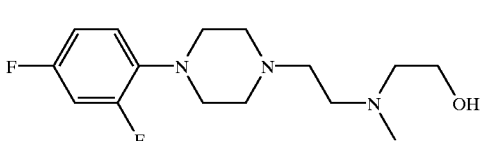 | 519 |
| 5-16 | 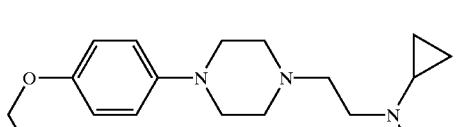 | 523 |
| 5-17 | 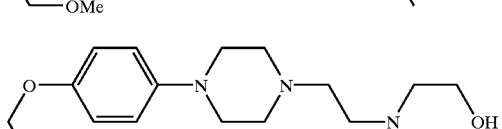 | 521 |
| 5-18 | 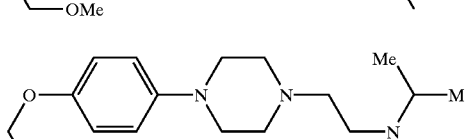 | 561 |
| 5-19 | 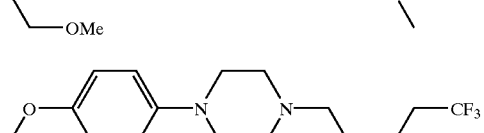 | 553, 555 |

-continued
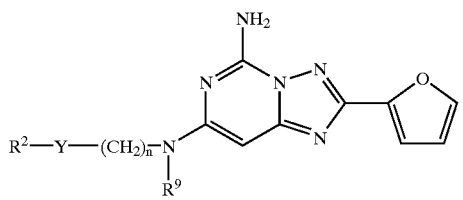
| Example | R²—Y—(CH₂)ₙ—N(R⁹)— | MS m/e |
|---|---|---|
| 5-20 | 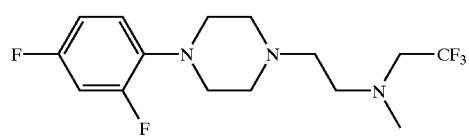 | 523 |
| 5-21 | 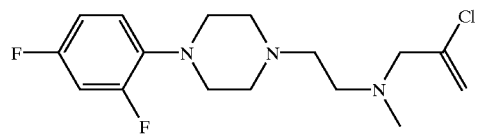 | 515, 517 |
| 5-22 | 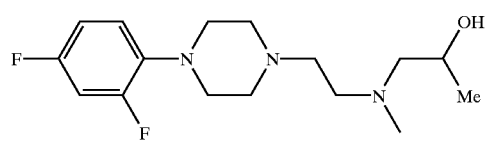 | 499 |
| 5-23 | 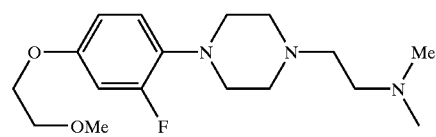 | 511 |
| 5-24 | 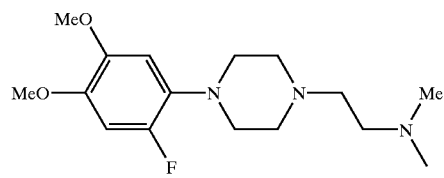 | 497 |
| 5-25 | 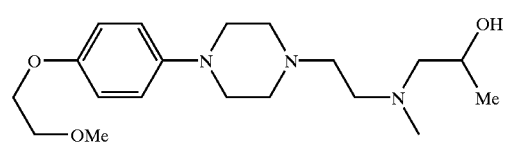 | 537 |

-continued
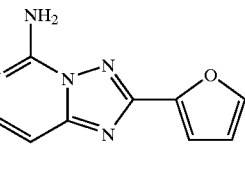
| Example | R²—Y—(CH₂)ₙ—N(R⁹)— | MS m/e |
|---|---|---|
| 5-26 | 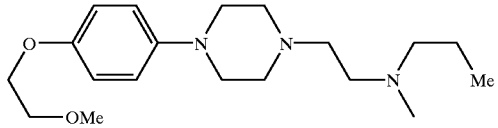 | 521 |
| 5-27 | 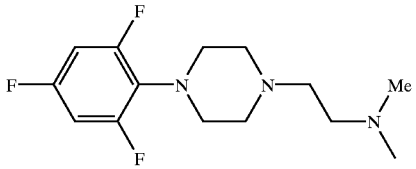 | 473 |
| 5-28 | 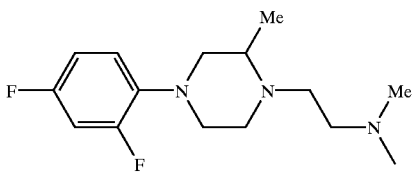 | 469 |
| 5-29 | 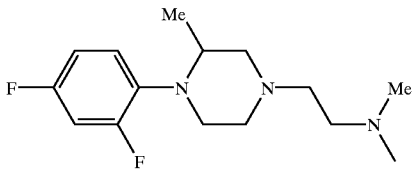 | 469 |
| 5-30 | 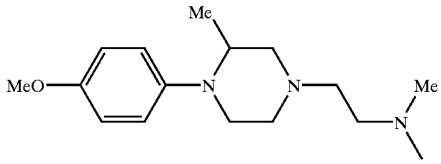 | 463 |
| 5-31 | 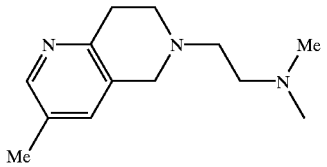 | 405 |
| 5-32 | 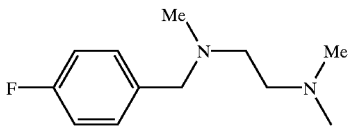 | 396 |
| 5-33 | 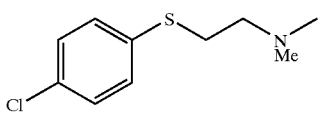 | 401, 403 |

-continued
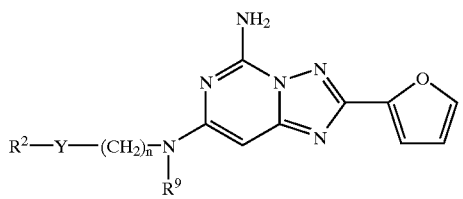
| Example | R²—Y—(CH₂)ₙ—N(R⁹)— | MS m/e |
|---|---|---|
| 5-34 | 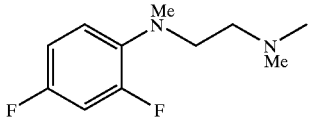 | 400 |
| 5-35 | 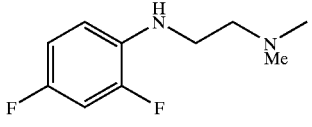 | 386 |
| 5-36 | 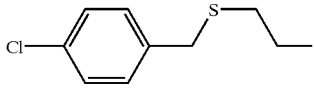 | 415, 417 |
| 5-37 | 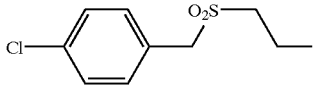 | 447, 449 |
| 5-38 | 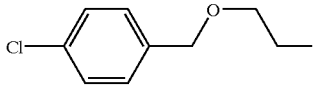 | 399, 401 |
| 5-39 | 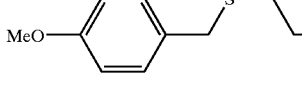 | 411 |
| 5-40 | 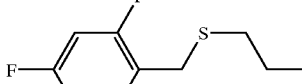 | 417 |
| 5-41 | 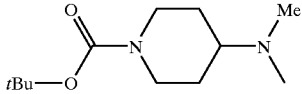 | 414 |
| 5-42 | 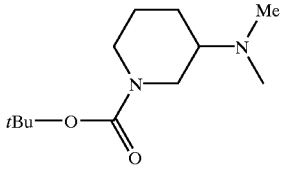 | 414 |
| 5-43 | 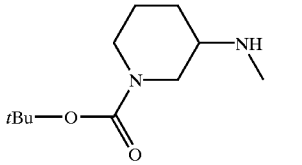 | 400 |

In a similar fashion, employ 2-amino-4,5,6-trichloropyrimidine as starting material to obtain Example 5-44 as a yellow solid.

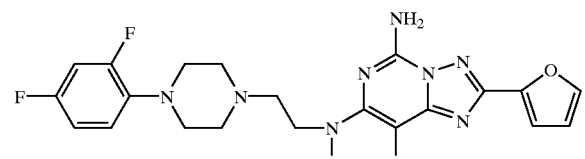

5-44: MS m/e 489, 491 (M + 1)

EXAMPLE 6

Step 4: To a solution of 3-cyanobenzoic acid (0.047 g, 0.32 mmol) in DMF (3 ml) add the product of Step 3 (0.110 g, 0.26 mmol), EDCl (0.061 g, 0.32 mmol), HOBt.H₂O (0.043 g, 0.32 mmol), and NMM (0.035 ml, 0.32 mmol). Stir 3 h, concentrate, and purify by PLC to obtain the product as a yellow solid.

Step 5: Add the product of Step 4 (0.101 g, 0.18 mmol) to BSA (6.0 ml). Heat at 120° C. 18 h, allow to cool, concentrate, add MeOH (20 ml), stir 0.5 h, concentrate, and purify by PLC to obtain the title compound as a yellow solid, MS: m/e 528 (M+1).

In a similar fashion, employ the product of Preparation 3 as starting material to obtain Example 6-2 as a white solid.

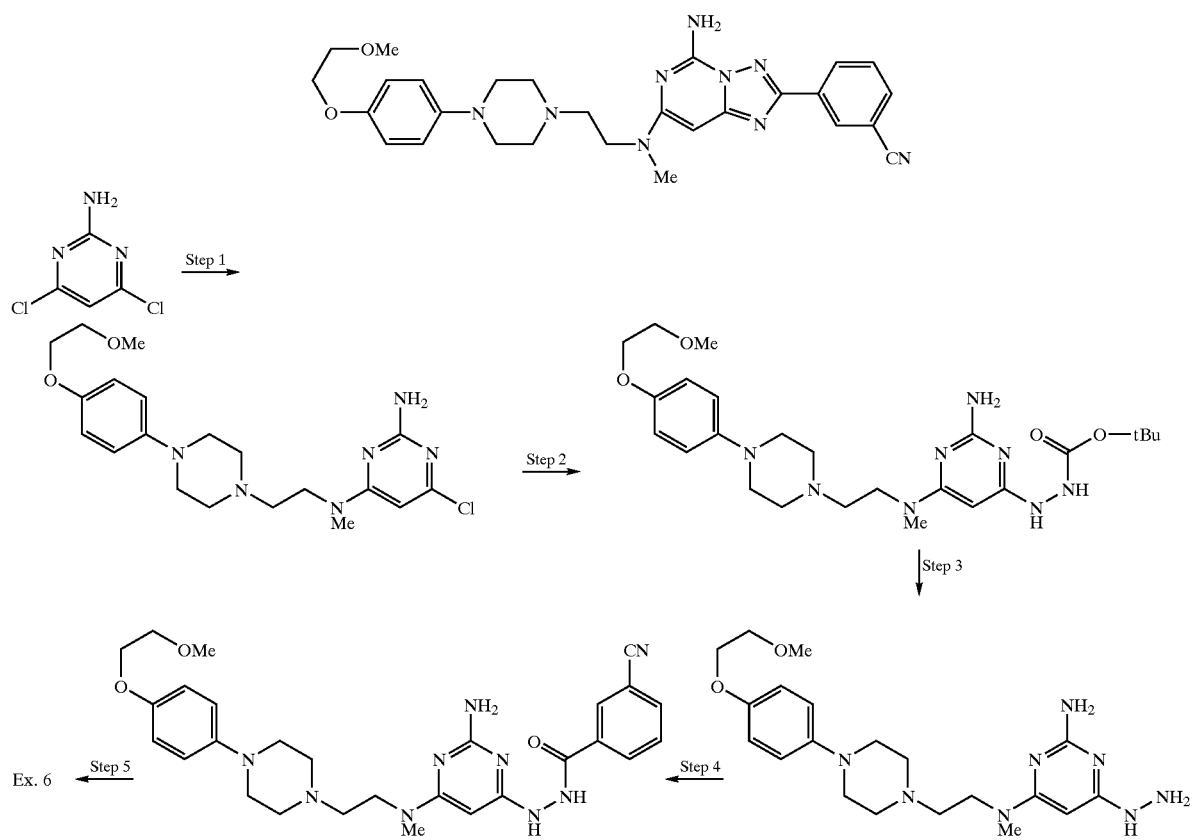

Step 1: Combine 2-amino-4,6-dichloropyrimidine (0.477 g, 2.73 mmol), the product of Preparation 3-2 (0.800 g, 2.73 mmol) and DIPEA (0.57 ml, 3.27 mmole) in DMF (5 ml). Heat in a sealed tube at 90° C. 14 h. Allow to cool, concentrate, and chromatograph on silica to obtain the product as a yellow solid.

Step 2: Combine the product of Step 1 (1.07 g, 2.54 mmol), t-butyl carbazate (1.01 g, 7.61 mmol) and 4.0M HCl/dioxane (0.76 ml, 3.04 mmol e) in EtOH (12 ml). Heat in a sealed tube at 100° C. 18 h, allow to cool, and add 2N NH)MeOH M (10 ml). Concentrate and chromatograph on silica to obtain the product as a yellow solid.

Step 3: Dissolve the product of Step 2 (0.90 g, 1.74 mmol) in CH₂Cl₂—MeOH (1:17, 20 ml). Add 4.0M HCl/dioxane (5.0 ml, 20 mmole). Stir 18 h, concentrate, add 1N NaOH (10 ml), and extract with CH₂Cl₂. Dry (MgSO₄), concentrate, and chromatograph on silica to obtain the product as a yellow solid.

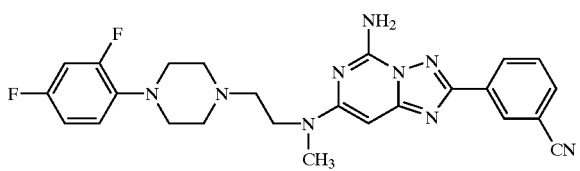

EX. 6-2: MS: m/e 490 (M + 1)

EXAMPLE 7

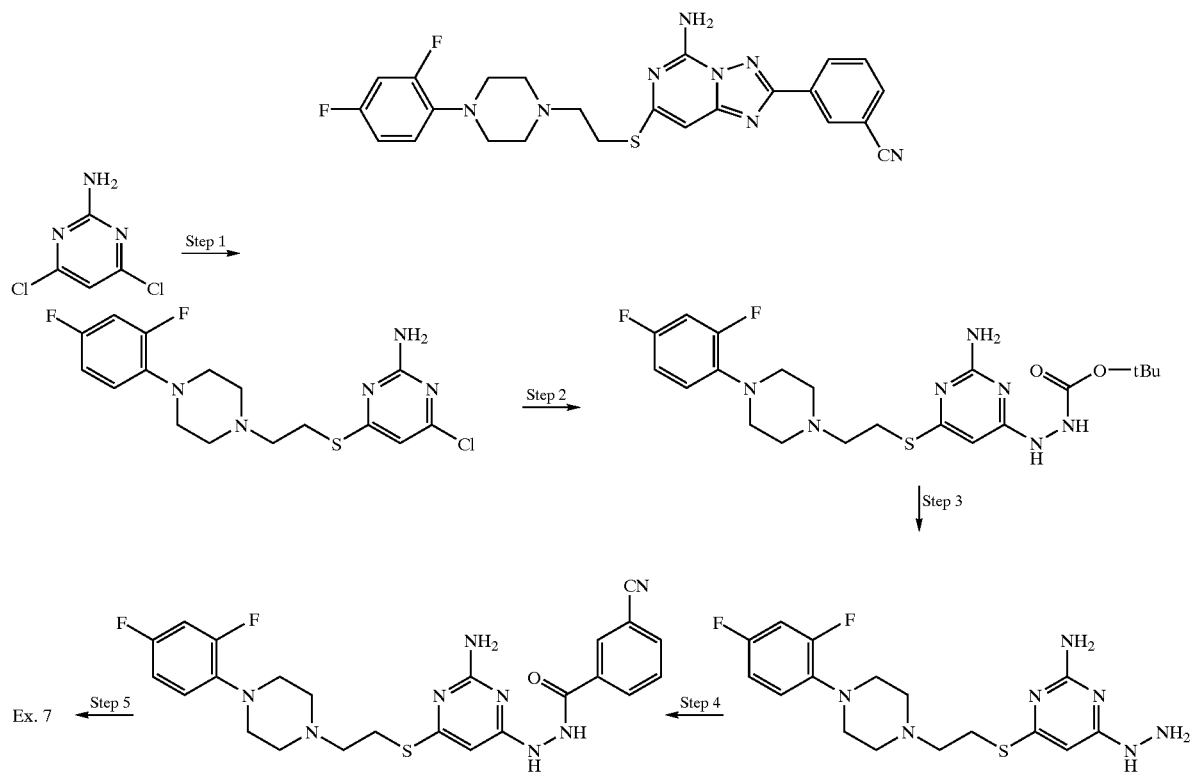

Step 1: Combine 2-amino-4,6-dichloropyrimidine (0.515 g, 3.14 mmol) and Na$_2$S (0.294 g, 3.76 mmole) in DMF (3 ml). Stir for 1 h. Add the product of Preparation 3, Step 1 (0.900 g, 3.45 mmol) in DMF (2 ml) and heat at 80° C. 18 h. Allow to cool, add CH$_2$Cl$_2$, and filter. Concentrate and chromatograph on silica to obtain the product as a yellow solid.

Steps 2–5: Treat the product of Step 1 according to Example 6, Steps 2–5, to obtain the title compound as an off-white solid, MS: m/e 493 (M+1).

EXAMPLE 8

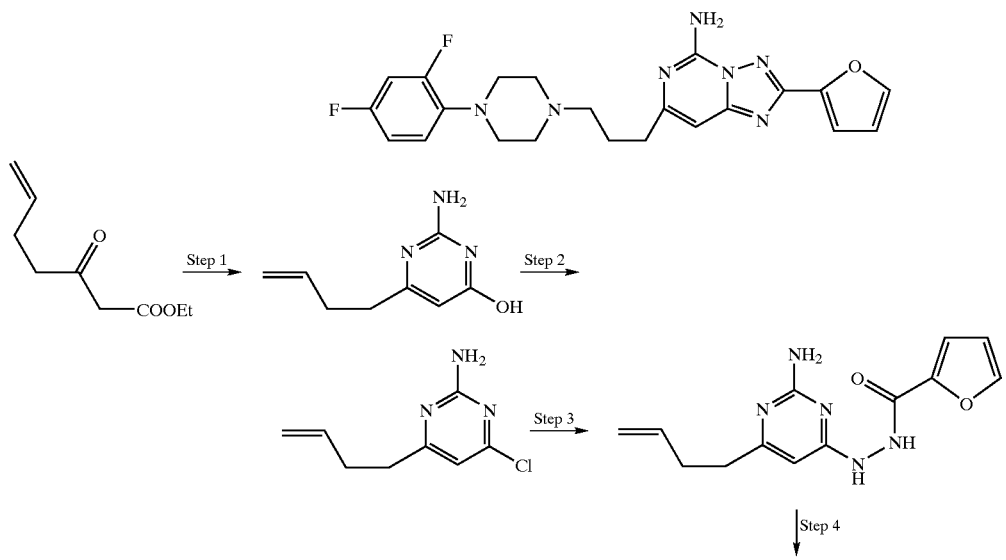

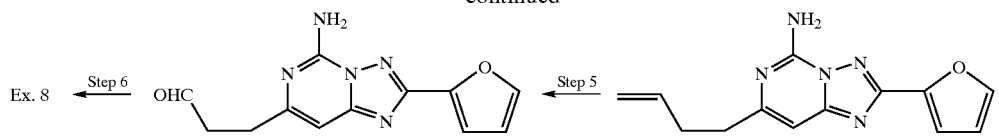

Step 1: Combine ethyl 3-oxo-6-heptenoate (6.68 g, 39.2 mmol) and guanidine carbonate (12.7 g, 70.6 mmol) in EtOH (100 ml). Heat at reflux 20 h, allow to cool, and add CH₂Cl₂ (100 ml). Filter, concentrate, and chromatograph on silica to obtain a white solid.

Step 2: Treat the product of Step 1 (2.35 g, 14.2 mmol) with POCl₃ (20 ml). Heat at reflux 2 h, concentrate, pour onto ice water, and basify with NaOH to pH9. Extract with CH₂Cl₂, dry (MgSO₄), concentrate, and chromatograph on silica to obtain a yellow oil.

Step 3: Combine the product of Step 2 (0.90 g, 4.9 mmol), 2-furoic hydrazide (0.865 g, 6.86 mmol) and 4.0M HCl/dioxane (1.47 ml, 5.88 mmol) in EtOH (10 ml). Heat in a sealed tube at 100° C. 18 h, allow to cool, and add 2N NH₃/MeOH (10 ml). Concentrate and chromatograph on silica to obtain the product as a yellow solid.

Step 4: Add the product of Step 3 (0.8 g, 2.9 mmol) to BSA (10 ml). Heat at 130° C. 6 h, allow to cool, and concentrate. Wash with water to obtain a yellow solid.

Step 5: Dissolve the product of Step 4 (0.10 g, 0.39 mmol) in THF (8 ml), cool in ice, add water (5 ml), then NaIO₄ (0.419 g, 1.96 mmol). Add two crystals OsO₄ and stir 5 h. Partition with CH₂Cl₂ and water, dry (MgSO₄), concentrate, and purify by PLC to obtain a yellow solid.

Step 6: Dissolve the product of Step 5 (0.080 g, 0.31 mmol) in CH₂Cl₂ (5 ml). Add 1-(2,4-difluorophenyl)piperazine (0.185 g, 0.93 mmol), AcOH (0.30 ml), and NaCNBH₃ (0.066 g, 0.31 mmol). Stir 18 h, concentrate, and purify by PLC to obtain the title compound as a white solid, MS: m/e=440 (M+1).

In a similar fashion, employ the appropriate aryl-piperazine to obtain Example 8-2 as a yellow powder.

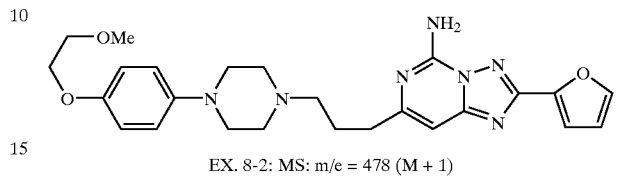

EX. 8-2: MS: m/e = 478 (M + 1)

EXAMPLE 9

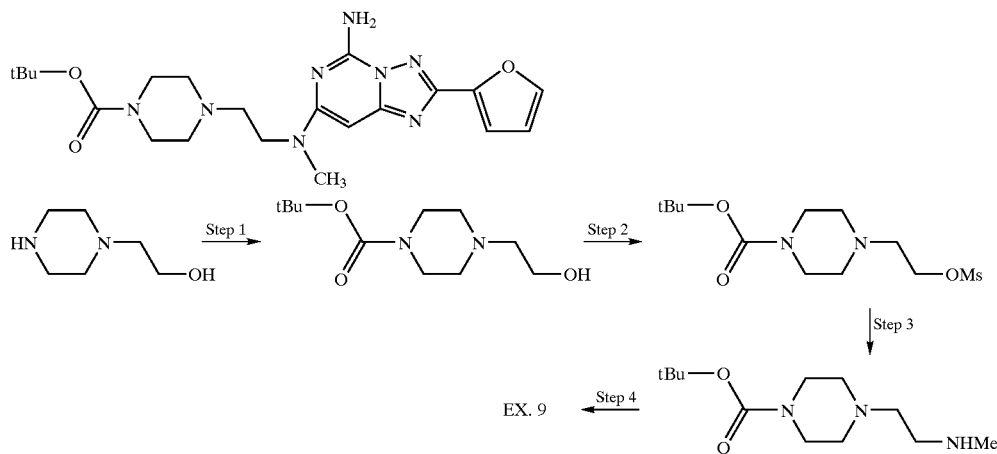

Step 1: Dissolve 1-(2-hydroxyethy)piperazine (3.25 g, 25 mmol) in THF (40 ml) and cool in ice. Add, portionwise, Boc₂O (5.45 g, 25 mmol). Allow to warm, stir 3 h, concentrate, and treat with hot hexane (50 ml). Cool to −15° C. and decant the hexane to leave a viscous orange oil.

Step 2: Combine the product of Step 1 (3.49 g, 15.0 mmol) and Et₃N (1.72 g, 17.0 mmol) in CH₂Cl₂ (40 ml) and cool in ice. Add, dropwise, MsCl (1.96 g, 17.0 mmol) in CH₂Cl₂ (10 ml). Allow to warm, stir 0.5 h, and concentrate. Partition between Et₂O and water, dry (MgSO₄) and concentrate to give the crude product as viscous oil with solid.

Step 3: Combine the crude product of Step 2 (4.6 g, ~15 mmol) with 40% aqueous MeNH₂ (35 g, 0.45 mol) and EtOH (35 ml). After 1 h, concentrate and partition between CH₂Cl₂ and 1N NaOH. Dry (MgSO₄) and concentrate to obtain the crude product as a yellow oil.

Step 4: Combine the crude product of Step 3 (0.46 g, ~1.5 mmol) with the product of Example 5, Step 2 (0.236 g, 1.00 mmol), and K₂CO₃ (0.207 g, 1.50 mmol) in DMF (8 ml). Heat in a sealed tube at 130° C. 18 h, concentrate and partition between EtOAC (10% MeOH) and water. Dry (MgSO₄), concentrate and chromatograph on silica and triturate with Et₂O to obtain the title compound as yellow solid, MS: m/e=443 (M+1).

EXAMPLE 10

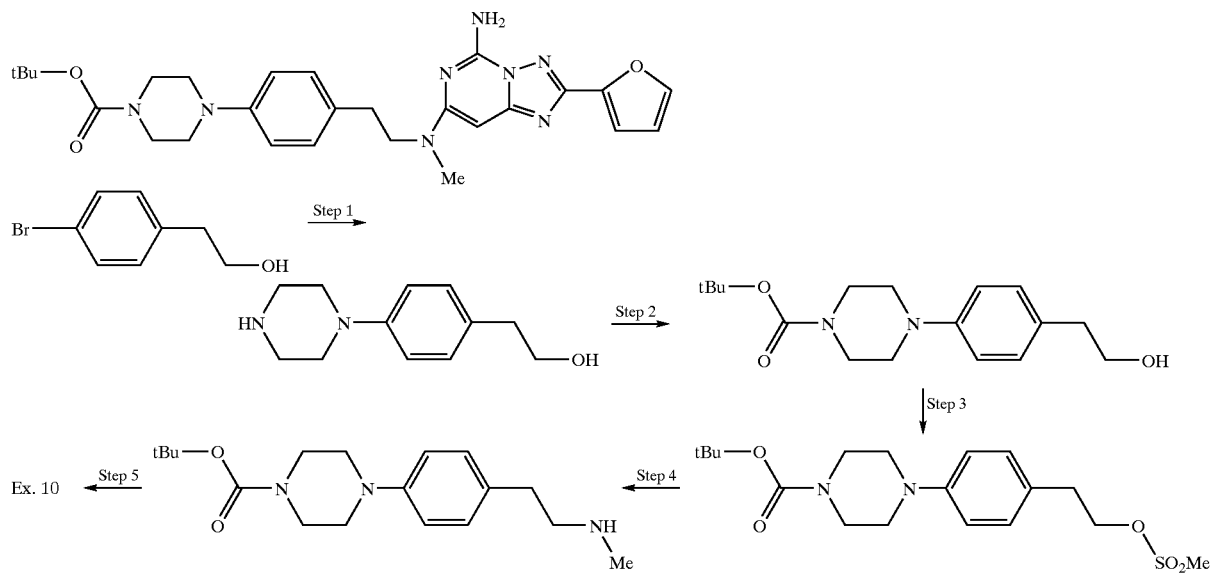

Step 1: Combine 2-(4-bromophenyl)ethanol (4.88 g, 24.3 mmol), piperazine (12.5 g, 146 mmol), NaO-tBu (3.27 g, 34.0 mmol), ±-BINAP (0.91 g, 1.5 mmol), and Pd$_2$(dba)$_3$ (0.28 g, 0.49 mmol) in toluene (40 ml). Heat at reflux 2 h, allow to cool, and extract with 1N HCl (4×50 ml). Basify with NaOH to pH 13 and extract with CH$_2$Cl$_2$. Dry (MgSO$_4$) and concentrate to give a brown oil.

Step 2: Dissolve the product of Step 1 (4.02 g, 19.5 mmol) in CH$_2$Cl$_2$ (50 ml). Add Boc$_2$O (4.51 g, 20.5 mmol) and then Et$_3$N (3.26 ml, 23.4 mmol). Stir 1 h and wash with 1N NaOH. Dry (MgSO$_4$), concentrate and chromatograph on silica to obtain a brown oil.

Step 3: Combine the product of Step 2 (1.00 g, 3.26 mmol) and Et$_3$N (0.73 ml, 5.2 mmol) in CH$_2$Cl$_2$ (20 ml). Cool in ice and add gradually MsCl (0.30 ml, 3.9 mmol). Stir 1 h, wash with sat. NaHCO$_3$, dry (MgSO$_4$) and concentrate to obtain a yellow oil.

Step 4: Dissolve the product of Step 3 (1.15 g, 2.99 mmol) in EtOH (10 ml). Add 40% aqueous MeNH$_2$ (10 ml) and heat in a sealed tube at 100° C. 16 h, allow to cool, concentrate, and partition between CH$_2$Cl$_2$ and 1N NaOH. Dry (MgSO$_4$), concentrate, and purify by PLC to obtain a yellow oil.

Step 5: Combine the product of Step 4 (0.466 g, 1.46 mmol), the product of Example 5, Step 2 (0.229 g, 0.97 mmol), and K$_2$CO$_3$ (0.202 g, 1.46 mmol) in DMF (8 ml). Heat in a sealed tube at 140° C. 18 h, concentrate and purify on PLC to obtain the title compound as a yellow foam, concentrate, and purify by PLC to obtain the product as a yellow oil MS: m/e=519 (M+1).

EXAMPLE 11

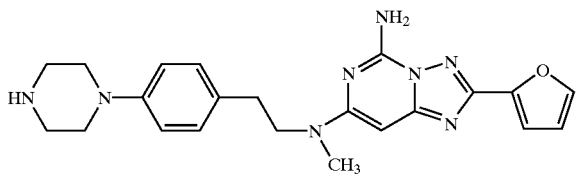

Dissolve the compound of Example 10 (0.215 g, 0.41 mmol) in 1:1 CH$_2$Cl$_2$—MeOH (10 ml) and add 4M HCl/dioxane (2.0 ml). Stir 18 h and add 7M NH$_3$/MeOH (4.0 ml). Concentrate, and chromatograph on silica to obtain the product as a white foam, MS: m/e=419 (M+1).

EXAMPLE 12

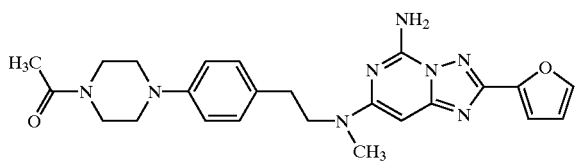

Dissolve the compound of Example 11 (0.050 g, 0.12 mmol) in CH$_2$Cl$_2$ (5 ml). Add DIPEA (0.031 ml, 0.18 mmol) and AcCl (0.010 ml, 0.14 mmol). Stir 1 h, concentrate, and purify by PLC to obtain the title compound as a white foam, MS: m/e=461 (M+1).

EXAMPLE 13

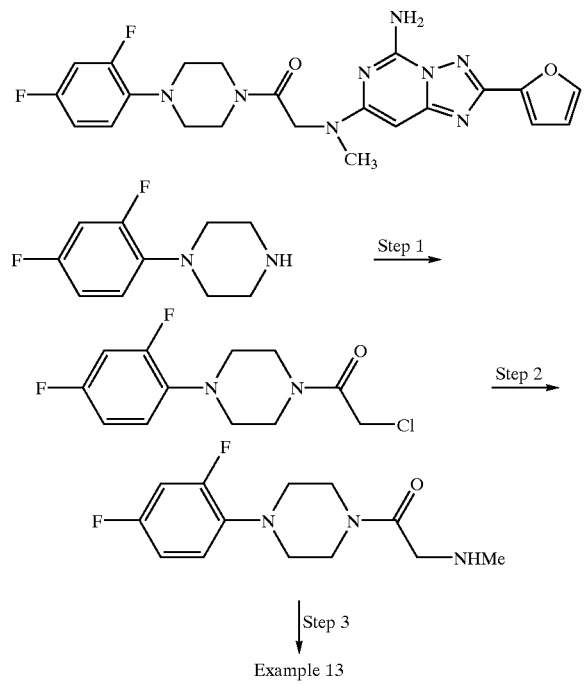

Example 13

Step 1: Dissolve 1-(2,4-difluorophenyl)piperazine (1.00 g, 5.05 mmol) in $CH_2Cl_2$ (5 ml). Cool in ice and add N-methylmorpholine (0.66 ml, 6.05 mmol) together with chloroacetyl chloride (0.45 ml, 5.6 mmol). Stir 2 h, concentrate, and partition between EtOAc and water. Dry ($MgSO_4$) and concentrate to obtain a yellow oil.

Step 2: Dissolve the product of Step 1 (1.49 g, 5.4 mmol) in EtOH (10 ml). Add 40% aqueous $MeNH_2$ (15 ml) and heat in a sealed tube at 100° C. 48 h, allow to cool, concentrate, and partition between $CH_2Cl_2$ and 1N NaOH. Dry ($MgSO_4$) and concentrate to obtain a yellow oil.

Step 3: Combine the product of Step 2 (0.137 g, 0.51 mmol), the product of Example 5, Step 2 (0.080 g, 0.34 mmol), and $K_2CO_3$ (0.070 g, 0.51 mmol) in DMF (4 ml). Heat in a sealed tube at 140° C. 18 h, concentrate and purify on PLC to obtain the title compound as a yellow foam, concentrate, and purify by PLC to obtain the product as a yellow solid MS: m/e=469 (M+1).

In similar fashion, using 2-bromopropionyl bromide in Step 1, prepare Example 13-2 as an off-white powder.

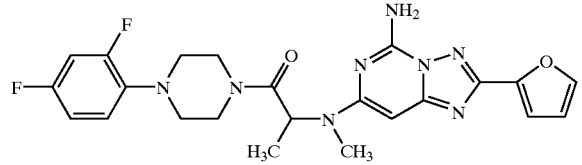

Ex. 13-2: MS: m/e = 483 (M + 1)

EXAMPLE 14

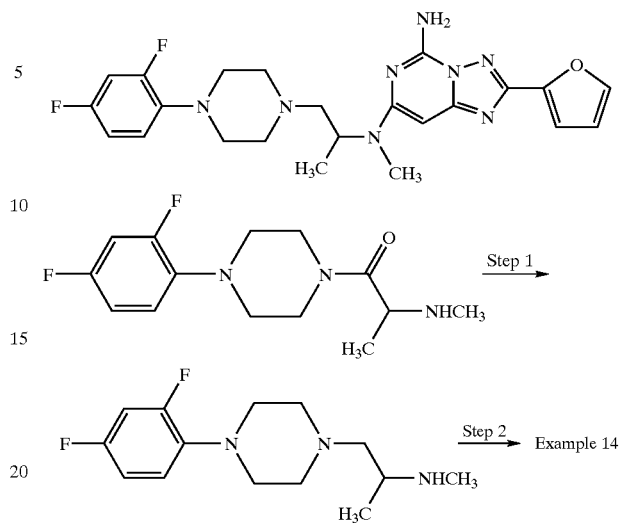

Step 1: Dissolve the product of Example 13-2, Step 2 (0.405 g, 1.43 mmol) in THF (10 ml). Add 1.0M $LiAlH_4/Et_2O$ (0.86 ml, 0.86 mmol). Heat at 60° C. 4 h, allow to cool, add water (0.065 ml), then 15% NaOH (0.065 ml), then water (3×0.065 ml). Filter and concentrate. Partition between $CH_2Cl_2$ and 1N HCl. Basify the aqueous to pH 12 with NaOH, extract with $CH_2Cl_2$, dry ($MgSO_4$) and concentrate. Purify by PLC to obtain a colorless oil.

Step 2: Treat the product of Step 1 with the product of Example 5, Step 2, following the procedure of Example 13, Step 3, to obtain the title compound as a yellow oil, MS: m/e=469 (M+1).

EXAMPLE 15

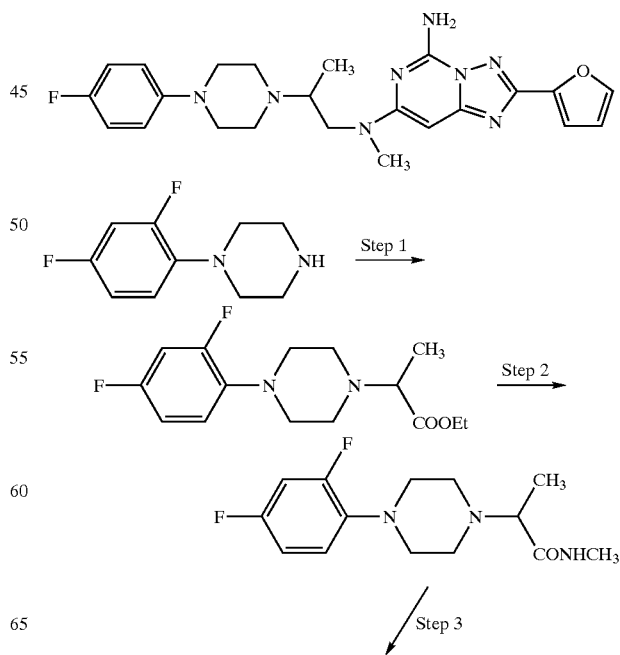

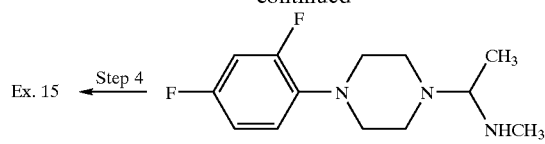

Step 1: Combine 1-(2,4-difluorophenyl)piperazine (1.98 g, 10.0 mmol), ethyl 2-bromo-propionate (1.81 g, 10.0 mmol), and K₂CO₃ (1.38 g, 10.0 mmol) in EtOH (15 ml). Heat at 80° C. 18 h, add more bromide (0.07 g), heat another 5 h, allow to cool, filter, and concentrate. Partition between Et₂O and water. Dry (MgSO₄) and concentrate to obtain a colorless liquid.

Step 2: Combine the product of Step 1 (2.38 g, 8.0 mmol) with 40% aqueous MeNH₂ (9.3 g, 0.12 mol) and EtOH (5 ml). Heat in a sealed tube at 80° C. 18 h, allow to cool, concentrate, and partition between EtOAc and water. Dry (MgSO₄) and concentrate to obtain a yellow solid. Recrystallization from MeOH-water gives white needles, m.p. 112-3° C.

Step 3: Treat the product of Step 2 with LiAlH₄ as in Example 14, Step 1 (24 h heating) to obtain a yellow oil.

Step 4: Treat the product of Step 3 with the product of Example 5, Step 2, following the procedure of Example 13, Step 3), to obtain the title compound as a colorless oil, MS: m/e=451 (M+1).

EXAMPLE 16

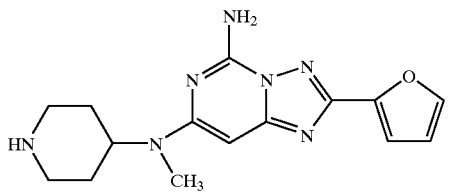

Dissolve the compound of Example 5–41 (0.206 g, 0.50 mmol) in 1:1 MeOH—CH₂Cl₂ (10 ml). Add 4.0M HCl/dioxane (4.0 ml). Stir 2 h and quench with 2M NH₃/MeOH. Concentrate and chromatograph on silica to obtain the title compound as a yellow oil, MS: m/e 314 (M+1).

In a similar manner prepare Examples 16-2 and 16-3.

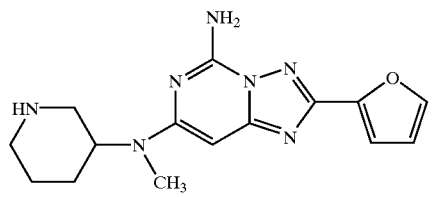

Ex. 16-2: MS: m/e 314 (M + 1)

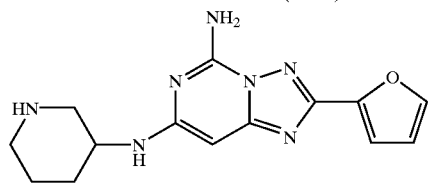

Ex. 16-3: MS: m/e 300 (M + 1)

EXAMPLE 17

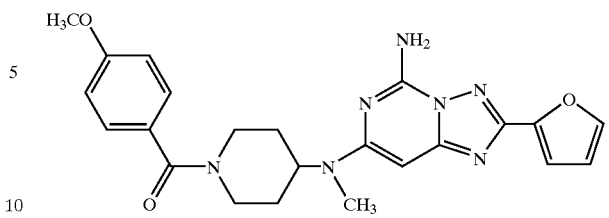

Combine the compound of Example 16 (0.070 g, 0.22 mmol), 4-methoxybenzoyl chloride (0.058 g, 0.34 mmol), and DIPEA (0.058 g, 0.45 mmol) in DMF (4 ml). Stir 2 h, concentrate, and purify by PLC to obtain the title compound as a yellow solid, MS: m/e 448 (M+1).

In similar fashion, convert the respective compounds of Example 16 to Examples 17-2 and 17-3.

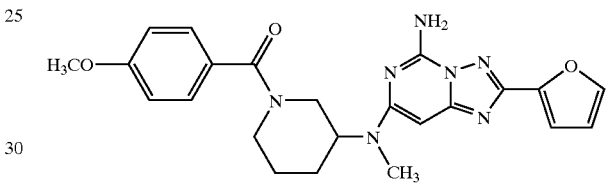

Ex. 17-2: MS: m/e 448 (M + 1)

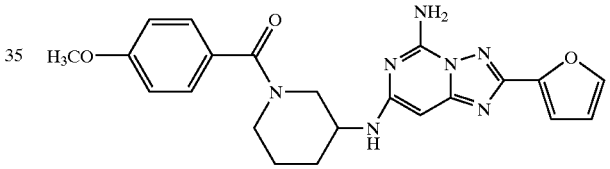

Ex. 17-3: MS: m/e 434 (M + 1)

EXAMPLE 18

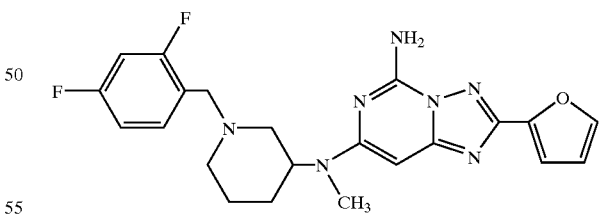

Combine the compound of Example 17-2 (0.119 g, 0.38 mmol), 2,4-difluoro-benzaldehyde (0.054 g, 0.38 mmol) and NaBH(OAc)₃ (0.157 g, 0.74 mmol) in CH₂Cl₂ (10 ml). Stir 3 h and add more aldehyde (0.016 g) and borohydride (0.045 g). Stir 18 h, dilute with CH₂Cl₂, and wash with sat. NaHCO₃, then brine. Dry (MgSO₄) and concentrate. Purify on PLC to obtain the title compound as a colorless oil, MS: m/e 440 (M+1).

EXAMPLE 19

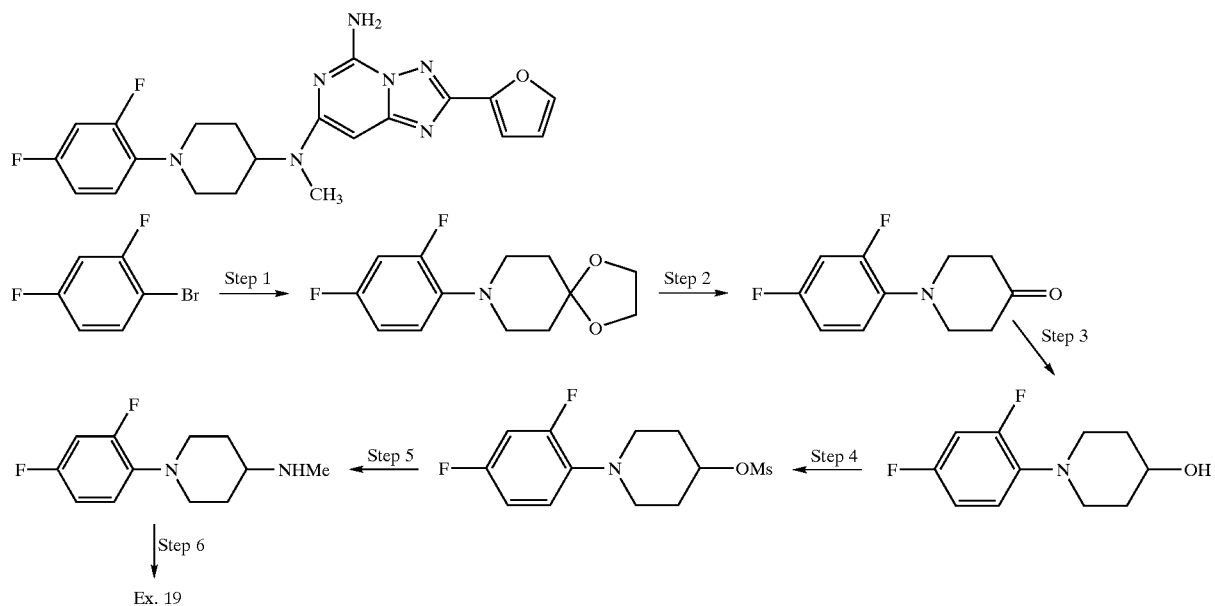

Step 1: Combine 2,4-difluorobromobezene (2.00 g, 10.4 mmol), 4-piperazinone ethylene ketal (2.27 g, 15.5 mmol), NaO-tBu (1.39 g, 14.5 mmol), ±-BINAP (0.387 g, 0.65 mmol), and $Pd_2(dba)_3$ (0.119 g, 0.21 mmol) in toluene (20 ml). Heat at reflux 18 h, allow to cool, and oncentrate. Chromatograph on silica to obtain a brown oil.

Step 2: Combine the product of Step 1 (2.55 g, 1 0.0 mmol) and 5N HCl (40 ml) in THF (25 ml). Stir 5 d and basify with $NH_4OH$. Concentrate and partition between $CH_2Cl_2$ and water. Wash with brine, dry ($MgSO_4$) and concentrate to obtain a brown oil.

Step 3: Cool the product of Step 2 (1.75 g, 8.3 mmol) in MeOH (15 ml) in ice and add $NaBH_4$ (0.16 g, 4.1 mmol). Stir 1 h, pour on ice and extract with $CH_2Cl_2$. Wash with brine, dry ($MgSO_4$) and concentrate to obtain a yellow oil.

Step 4: Combine the product of Step 3 (1.65 g, 7.7 mmol) and $Et_3N$ in $CH_2Cl_2$ (30 ml). Cool in ice and add methanesulfonyl chloride (1.07 g, 9.4 mmol). Stir 1 h and wash with sat. $NaHCO_3$. Dry ($MgSO_4$) and concentrate to obtain a yellow oil.

Step 5: Dissolve the product of Step 4 (1.00 g, 3.4 mmol) in EtOH (10 ml). Add 40% aqueous $MeNH_2$ (20 ml, 0.2 mol). Heat in a sealed tube at 100° C. for 3 h, allow to cool, and concentrate. Partition between $CH_2Cl_2$ and water. Wash with brine, dry ($MgSO_4$) and concentrate. Purify on PLC to obtain a yellow oil.

Step 6: Combine the product of Step 5 (0.035 g, 0.15 mmol) with the product of Example 5, Step 2 (0.041 mg, 0.18 mmol) and $K_2CO_3$ (0.031 g, 0.23 mmol) in DMF (3 ml). Heat at 140° C. for 18 h. Concentrate and purify by PLC to obtain the title compound as a colorless gum, MS: m/e 426 (M+1).

Because of their adenosine $A_{2a}$ receptor antagonist activity, compounds of the present invention are useful in the treatment of depression, cognitive function diseases and neurodegenerative diseases such as Parkinson's disease, senile dementia as in Alzheimer's disease, and psychoses of organic origin. In particular, the compounds of the present invention can improve motor-impairment due to neurodegenerative diseases such as Parkinson's disease.

The other agents known to be useful in the treatment of Parkinson's disease that can be administered in combination with the compounds of formula I include: L-DOPA; dopaminergic agonists such as quinpirole, ropinirole, pramipexole, pergolide and bromocriptine; MAO-B inhibitors such as deprenyl and selegiline; DOPA decarboxylase inhibitors such as carbidopa and benserazide; and COMT inhibitors such as tolcapone and entacapone. One to three other agents can be used in combination with the compounds of formula I, preferably one.

The pharmacological activity of the compounds of the invention was determined by the following in vitro and in vivo assays to measure $A_{2a}$ receptor activity.

Human Adenosine $A_{2a}$ and $A_1$ Receptor
Competition Binding Assay Protocol

Membrane Sources:

$A_{2a}$: Human $A_{2a}$ Adenosine Receptor membranes, Catalog #RB-HA2a, Receptor Biology, Inc., Beltsville, Md. Dilute to 17 μg/100 μl in membrane dilution buffer (see below).

Assay Buffers:

Membrane dilution buffer: Dulbecco's Phosphate Buffered Saline (Gibco/BRL)+10 mM $MgCl_2$.

Compound Dilution Buffer: Dulbecco's Phosphate Buffered Saline (Gibco/BRL)+10 mM $MgCl_2$ supplemented with 1.6 mg/ml methyl cellulose and 16% DMSO. Prepared fresh daily.

Ligands:

$A_{2a}$: [3H]-SCH 58261, custom synthesis, AmershamPharmacia Biotech, Piscataway, N.J. Stock is prepared at 1 nM in membrane dilution buffer. Final assay concentration is 0.5 nM.

$A_1$: [3H]-DPCPX, AmershamPharmacia Biotech, Piscataway, N.J. Stock is prepared at 2 nM in membrane dilution buffer. Final assay concentration is 1 nM.

Non-specific Binding:

$A_{2a}$: To determine non-specific binding, add 100 nM CGS 15923 (RBI, Natick, Mass.). Working stock is prepared at 400 nM in compound dilution buffer.

A₁: To determine non-specific binding, add 100 μM NECA (RBI, Natick, Mass.). Working stock is prepared at 400 μM in compound dilution buffer.

Compound Dilution:

Prepare 1 mM stock solutions of compounds in 100% DMSO. Dilute in compound dilution buffer. Test at 10 concentrations ranging from 3 μM to 30 pM. Prepare working solutions at 4× final concentration in compound dilution buffer.

Assay Procedure:

Perform assays in deep well 96 well plates. Total assay volume is 200 μl. Add 50 μl compound dilution buffer (total ligand binding) or 50 μl CGS 15923 working solution ($A_{2a}$ non-specific binding) or 50 μl NECA working solution ($A_1$ non-specific binding) or 50 μl of drug working solution. Add 50 μl ligand stock ([3H]-SCH 58261 for $A_{2a}$, [3H]-DPCPX for $A_1$). Add 100 μl of diluted membranes containing the appropriate receptor. Mix. Incubate at room temperature for 90 minutes. Harvest using a Brandel cell harvester onto Packard GF/B filter plates. Add 45 μl Microscint 20 (Packard), and count using the Packard TopCount Microscintillation Counter. Determine $IC_{50}$ values by fitting the displacement curves using an iterative curve fitting program (Excel). Determine Ki values using the Cheng-Prusoff equation.

Haloperidol-induced Catalepsy in the Rat

Male Sprague-Dawley rats (Charles River, Calco, Italy) weighing 175–200 g are used. The cataleptic state is induced by the subcutaneous administration of the dopamine receptor antagonist haloperidol (1 mg/kg, sc), 90 min before testing the animals on the vertical grid test. For this test, the rats are placed on the wire mesh cover of a 25×43 plexiglass cage placed at an angle of about 70 degrees with the bench table. The rat is placed on the grid with all four legs abducted and extended ("frog posture"). The use of such an unnatural posture is essential for the specificity of this test for catalepsy. The time span from placement of the paws until the first complete removal of one paw (decent latency) is measured maximally for 120 sec.

The selective $A_{2A}$ adenosine antagonists under evaluation are administered orally at doses ranging between 0.3 and 3 mg/kg, 1 and 4 h before scoring the animals.

6-OHDA Lesion of the Middle Forebrain Bundle in Rats

Adult male Sprague-Dowley rats (Charles River, Calco, Como, Italy), weighing 275–300 g, are used in all experiments. The rats are housed in groups of 4 per cage, with free access to food and water, under controlled temperature and 12 hour light/dark cycle. The day before the surgery the rats are fasted over night with water ad libitum.

Unilateral 6-hydroxydopamine (6-OHDA) lesion of the middle forebrain bundle is performed according to the method described in Ungerstedt et al, *Brian Research*, 24 (1970), p. 485–493, and Ungerstedt, *Eur. J. Pharmacol.*, 5 (1968), p. 107–110, with minor changes. Briefly, the animals are anaesthetized with chloral hydrate (400 mg/kg, ip) and treated with desipramine (10 mpk, ip) 30 min prior to 6-OHDA injection in order to block the uptake of the toxin by the noradrenergic terminals. Then, the animals are placed in a stereotaxic frame. The skin over the skull is reflected and the stereotaxic coordinates (−2.2 posterior from bregma (AP), +1.5 lateral from bregma (ML), 7.8 ventral from dura (DV) are taken, according to the atlas of Pellegrino et al (Pellegrino L. J., Pellegrino A. S. and Cushman A. J., *A Stereotaxic Atlas of the Rat Brain*, 1979, New York: Plenum Press). A burr hole is then placed in the skull over the lesion site and a needle, attached to a Hamilton syringe, is lowered into the left MFB. Then 8 μg 6-OHDA-HCl is dissolved in 4 μl of saline with 0.05% ascorbic acid as antioxidant, and infused at the constant flow rate of 1 μl/1 min using an infusion pump. The needle is withdrawn after additional 5 min and the surgical wound is closed and the animals left to recover for 2 weeks.

Two weeks after the lesion the rats are administered with L-DOPA (50 mg/kg, ip) plus Benserazide (25 mg/kg, ip) and selected on the basis of the number of full contralateral turns quantified in the 2 h testing period by automated rotameters (priming test). Any rat not showing at least 200 complete turns/2 h is not included in the study.

Selected rats receive the test drug 3 days after the priming test (maximal dopamine receptor supersensitivity). The new $A_{2A}$ receptor antagonists are administered orally at dose levels ranging between 0.1 and 3 mg/kg at different time points (i.e., 1, 6, 12 h) before the injection of a subthreshold dose of L-DOPA (4 mpk, ip) plus benserazide (4 mpk, ip) and the evaluation of turning behavior.

Using the above test procedures, the following results were obtained for preferred and/or representative compounds of the invention.

Results of the binding assay on compounds of the invention showed $A_{2a}$ Ki vaules of about 0.3 to about 50 nM, with preferred compounds showing Ki values between 0.3 and 10 nM.

Selectivity is determined by dividing Ki for A1 receptor by Ki for A2a receptor. Compounds of the invention have a selectivity ranging from about 1 to about 1600. Preferred are compounds are those wherein the selectivity is >100.

Preferred compounds showed about a 50–75% decrease in descent latency when tested orally at 1–3 mg/kg for anti-cataleptic activity in rats.

One to three compounds of formula I can be administered in the method of the invention, preferably one.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen for compounds of formula I is oral administration of from 10 mg to 2000 mg/day preferably 10 to 1000 mg/day, in two to four divided doses to provide relief from central nervous system diseases such as Parkinson's disease. The compounds are non-toxic when administered within this dosage range.

The doses and dosage regimen of the other agents used in the treatment of Parkinson's disease will be determined by the attending clinician in view of the approved doses and dosage regimen in the package insert, taking into consideration the age, sex and condition of the patient and the severity of the disease. It is expected that when the combination of a compound of formula I and a another anti-Parkinson's disease agent is administered, lower doses of the components will be effective compared to the doses of the components administered as monotherapy. When administered in combination, the compound(s) of formula I and the other agent(s) for treating Parkinson's disease can be administered simultaneously or sequentially. This is particularly useful when the components of the combination are preferably given on different dosing schedules, e.g., one component is administered daily and another every six hours, or when the preferred pharmaceutical compositions are different, e.g. one is preferably a tablet and one is a capsule. A kit comprising the separate dosage forms is therefore advantageous.

The following are examples of pharmaceutical dosage forms which contain a compound of the invention. Those skilled in the art will recognize that dosage forms can be modified to contain both a compound of formula I and a dopaminergic agent. The scope of the invention in its pharmaceutical composition aspect is not to be limited by the examples provided.

PHARMACEUTICAL DOSAGE FROM EXAMPLES

Example A-tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Examples B-capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound represented by the structural formula

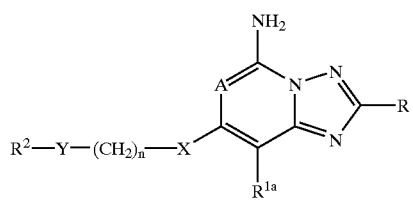

or a pharmaceutically acceptable salt thereof, wherein:

A is N;

$R^1$ and $R^{1a}$ are independently selected from the group consisting of H, $(C_1–C_6)$-alkyl, halo, CN and —$CF_3$;

Y is —O—, —S—, —SO—, —$SO_2$—, $R^5$-heteroaryldiyl, $R^5$-arylene or

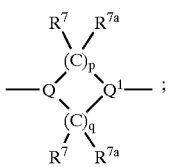

p and q are independently 2–3;

Q and $Q^1$ are independently selected from the group consisting of

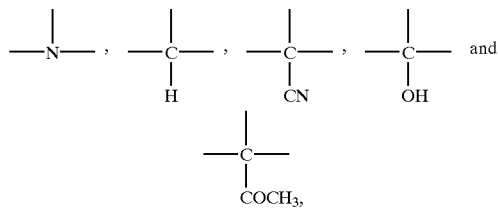

provided that at least one of Q and $Q^1$ is

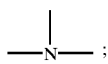

R is $R^5$-aryl, $R^5$-heteroaryl, $R^6$—$(C_2-C_6)$alkenyl or $R^8$-$(C_2-C_6)$alkynyl;

$R^2$ is $R^5$-aryl, $R^5$-heteroaryl, $R^5$-aryl$(C_1-C_6)$alkyl or $R^5$-heteroaryl$(C_1-C_6)$alkyl; or $R^2$—Y is

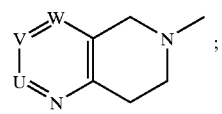

U, V, and W are independently selected from the group consisting of N and $CR^1$, provided that at least one of U, V and W is $CR^1$;

n is 1, 2 or 3; and (a) X is —N($R^9$)—, Y is $R^5$-arylene and $R^2$ is

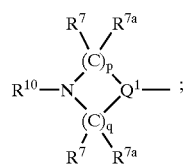

or n is 2 or 3; and (b) X is —C($R^3$)($R^{3a}$)—, —C(O)—, —O—, —S—, —SO—, —$SO_2$—, —N($R^9$)—, $R^4$-arylene or $R^4$-heteroaryldiyl; or Y is a bond and X is —C(O)—, —N($R^9$)—, $R^4$-arylene or $R^4$-heteroaryldiyl; or Y is —N($R^{9a}$)—, —C(O)N($R^{9a}$)— or —O—$(CH_2)_2$—N($R^{9a}$)—, and X is —N($R^9$)—; or X is —N($R^9$)—, and Y and $R^2$ together are

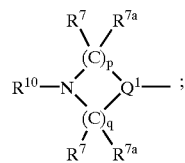

or n is 0; and (c) Y is a bond, X is —N($R^9$)—, and $R^2$ is

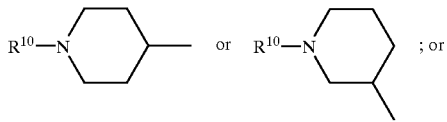

(d) X is —N($R^9$)— and Y and $R^2$ together are

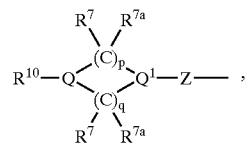

wherein Z is —C(O)—$CH_2$—, —C(O)—CH($C_1-C_8$ alkyl)—, —$CH_2$—CH($C_1-C_8$ alkyl)—, or —CH($C_1-C_6$ alkyl)—$CH_2$—;

$R^3$ and $R^{3a}$ are independently selected from the group consisting of H, —OH, $C_1-C_6$ alkyl, hydroxy$(C_1-C_6)$alkyl, $(C_1-C_6)$alkoxy$(C_1-C_6)$alkyl, amino$(C_1-C_6)$alkyl, $(C_1-C_6)$alkylamino$(C_1-C_6)$alkyl and di$(C_1-C_6)$alkylamino$(C_1-C_6)$alkyl;

$R^4$ is 1–3 substituents selected from the group consisting of H, $(C_1-C_6)$alkyl, —OH, $(C_1-C_6)$alkoxy, $(C_1-C_6)$alkoxy$(C_1-C_6)$alkoxy, halo, —$CF_3$, and —CN;

$R^5$ is 1–3 substituents independently selected from the group consisting of H, $(C_1-C_6)$alkyl, —OH, $(C_1-C_6)$alkoxy, $(C_1-C_6)$alkoxy$(C_1-C_6)$alkyl, $(C_1-C_6)$alkoxy$(C_1-C_6)$alkoxy, halo, —$CF_3$, —CN, —$NH_2$, $(C_1-C_6)$alkylamino, di$(C_1-C_6)$alkylamino, amino$(C_1-C_6)$alkyl, $(C_1-C_6)$alkylamino$(C_1-C_6)$alkyl, di$(C_1-C_6)$alkylamino$(C_1-C_6)$alkyl, $(C_1-C_6)$alkanoyl-amino, $(C_1-C_6)$alkanesulfonyiamino, $(C_1-C_6)$alkylthio, $(C_1-C_6)$alkylthio$(C_1-C_6)$alkyl, $R^6$—$(C_2-C_6)$alkenyl, $R^6$—$(C_2-C_6)$alkynyl, hydroxy$(C_1-C_6)$alkyl, $(C_1-C_6)$alkoxy-C(O)-amino, or heterocycloalkyl$(C_1-C_6)$alkyl;

$R_6$ is 1 to 3 substituents independently selected from the group consisting of H, $(C_1-C_6)$alkyl, —OH, $(C_1-C_6)$alkoxy and halo;

$R^7$ and $R^{7a}$ are independently selected from the group consisting of H, $(C_1-C_6)$alkyl, $(C_1-C_6)$alkoxy$(C_1-C_6)$alkyl, $R^6$-aryl and $R^6$-heteroaryl, or an $R^7$ and an $R^{7a}$ substituent on the same carbon can form =O;

$R^8$ is 1 to 3 substituents independently selected from H, $(C_1-C_6)$alkyl, —OH, $(C_1-C_6)$alkoxy, $(C_1-C_6)$alkoxy$(C_1-C_6)$alkoxy, halo, —$CF_3$, and —CN;

$R^9$ and $R^{9a}$ are independently selected from the group consisting of H, $(C_1-C_6)$alkyl, hydroxy$(C_2-C_6)$alkyl, $(C_1-C_6)$alkoxy$(C_2-C_6)$alkyl, amino$(C_2-C_6)$alkyl, $(C_1-C_6)$alkylamino$(C_2-C_6)$alkyl, di$(C_1-C_6)$alkylamino$(C_2-C_6)$alkyl, halo-$(C_3-C_6)$alkenyl, $CF_3$—$(C_1-C_6)$alkyl, $(C_3-C_6)$alkenyl, —$(C_3-C_6)$cycloalkyl and $(C_3-C_6)$cycloalkyl-$(C_1-C_6)$alkyl; and $R^{10}$ is H, —C(O)—O—($C_1$-$C_6$)alkyl, $R^5$-aryl, —C(O)—($C_1$-$C_6$)alkyl, —C(O)—($R^5$-aryl) or $R^5$-aryl-($C_1$-$C_6$)alkyl.

2. The compound of claim 1 wherein X is —O—, —S—, —N($R^9$)— or $R^4$-arylene.

3. The compound of claim 2 wherein $R^9$ is methyl or ethyl.

4. The compound of claim 1 wherein Y is a bond or piperazinyl.

5. The compound of claim 1 wherein $R^2$ is $R^5$-aryl.

6. The compound of claim 1 wherein R is furyl.

7. The compound of claim 1 wherein X is —O—, —S—, —N($R^9$)— or $R^4$-arylene; $R^9$ is methyl or ethyl; Y is a bond or piperazinyl; $R^2$ is $R^5$-aryl; and R is furyl.

8. The compound of claim 7 wherein $R^5$ is 1 or 2 substituents selected from the group consisting of H, ($C_1$-$C_6$)alkoxy, ($C_1$-$C_6$)alkoxy($C_1$-$C_6$)-alkoxy, halo and $CF_3$.

9. A compound of claim 1 selected from the group consisting of compounds of the formula

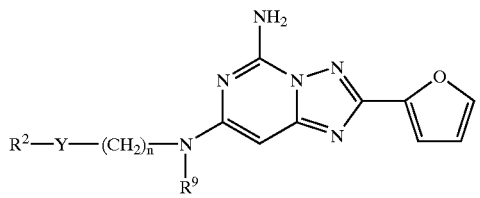

wherein $R^2$—Y—$(CH_2)_n$—N($R^9$)— is as defined in the table and Me means methyl:

| $R^2$—Y—$(CH_2)_n$—N($R^9$)— |
|---|
| 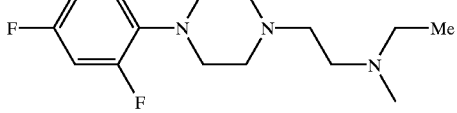 |
| 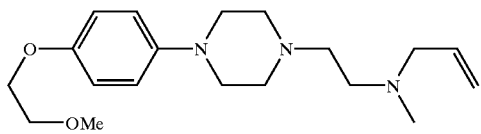 |
| 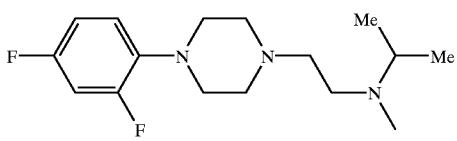 |
| 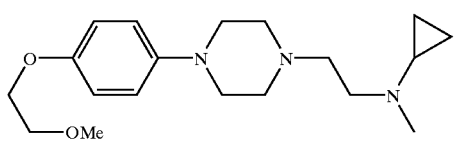 |
| 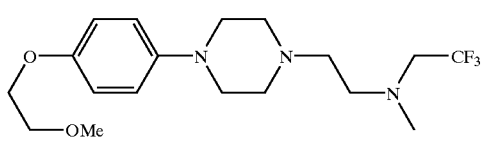 |
| 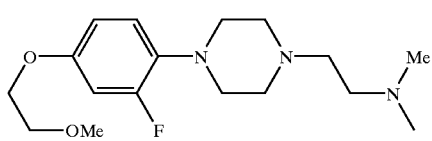 |
| 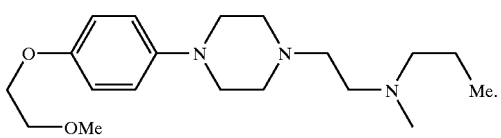 |

10. A pharmaceutical composition comprising a therapeutically effective amount of a compound of claim 1 in a pharmaceutically acceptable carrier.

11. A method of treating depression comprising administering an effective amount of a compound of claim 1 to a mammal in need of such treatment.

* * * * *

UNITED STATES PATENT AND TRADEMARK OFFICE
CERTIFICATE OF CORRECTION

PATENT NO. : 6,875,772 B2
DATED : April 5, 2005
INVENTOR(S) : Bernard R. Neustadt et al.

It is certified that error appears in the above-identified patent and that said Letters Patent is hereby corrected as shown below:

Title page,
Item [54], change "ADEONSINE" to -- ADENOSINE --.

Column 61,
Lines 34-35, change "$R^{8-}(C_2-C_6)$alkynyl" to -- $R^6-(C_2-C_6)$alkynyl --.

Column 62,
Lines 27-28, change "-C(O)-CH($C_1-C_8$ alkyl-, -$CH_2$-CH($C_1-C_8$ alkyl)-" to -- -C(O)-CH($C_1-C_6$ alky-, -$CH_2$-CH($C_1-C_6$ alkyl)- --.
Line 46, change "alkanesulfoniamino" to -- alkanesulfonylamino --.
Line 56, change "$R^6$-aryl and $R^8$-heteroaryl" to -- $R^8$-aryl and $R^8$-heteroaryl --.

Signed and Sealed this

Seventh Day of June, 2005

JON W. DUDAS
*Director of the United States Patent and Trademark Office*